(12) United States Patent
Morooka et al.

(10) Patent No.: US 10,073,255 B2
(45) Date of Patent: Sep. 11, 2018

(54) SINGLE FOCAL LENGTH LENS AND OPTICAL APPARATUS USING THE SAME

(71) Applicant: OLYMPUS CORPORATION, Hachioji-shi, Tokyo (JP)

(72) Inventors: Masaru Morooka, Akishima (JP); Kenichi Nagasawa, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/494,687

(22) Filed: Apr. 24, 2017

(65) Prior Publication Data

US 2018/0031813 A1  Feb. 1, 2018

(30) Foreign Application Priority Data

Aug. 1, 2016 (JP) .................................. 2016-151091

(51) Int. Cl.

| G02B 9/34 | (2006.01) |
|---|---|
| G02B 15/22 | (2006.01) |
| A61B 1/00 | (2006.01) |
| A61B 1/005 | (2006.01) |
| A61B 1/04 | (2006.01) |

(Continued)

(52) U.S. Cl.
CPC .............. *G02B 15/22* (2013.01); *A61B 1/005* (2013.01); *A61B 1/00039* (2013.01); 
(Continued)

(58) Field of Classification Search
CPC ... G02B 9/00; G02B 9/34; G02B 9/60; G02B 9/62; G02B 9/64; G02B 13/00; G02B 13/001; G02B 13/0015; G02B 13/004; G02B 13/0045; G02B 13/24; G02B 13/26; G02B 15/00; G02B 15/22; G02B 21/241; G02B 21/361; G02B 21/142; G02B 23/2438; G02B 23/2469; H04N 5/2254; H04N 5/2256; H04N 5/23293

See application file for complete search history.

(56) References Cited

U.S. PATENT DOCUMENTS

| 8,503,096 B2 | 8/2013 | Imaoka et al. |
|---|---|---|
| 8,643,960 B2 | 2/2014 | Hayashi et al. |

(Continued)

FOREIGN PATENT DOCUMENTS

| JP | 2012220654 A | 11/2012 |
|---|---|---|
| JP | 2012226309 A | 11/2012 |

(Continued)

*Primary Examiner* — Thong Nguyen
(74) *Attorney, Agent, or Firm* — Holtz, Holtz & Volek PC

(57) ABSTRACT

A single focal length lens includes an aperture stop and first through fourth lens units having, respectively, negative refractive power, positive refractive power, negative refractive power, and positive refractive power. Positions of the first, second, and fourth lens units are fixed. When focusing from an object at infinity to an object at a short distance, the third lens unit moves toward the image side. Conditional expressions (1), (2), and (3) are satisfied:

$$-5 < f1/f < -0.5 \quad (1),$$

$$-10 < f3/f < -1 \quad (2), \text{ and}$$

$$0.5 < f12/f < 1 \quad (3),$$

where f1 denotes a focal length of the first lens unit, f denotes a focal length of an overall single focal length lens system when focusing to an object at infinity, f3 denotes a focal length of the third lens unit, and f12 denotes a combined focal length of the first and second lens units.

15 Claims, 16 Drawing Sheets

(51) Int. Cl.
*G01J 1/08* (2006.01)
*G02B 21/24* (2006.01)
*G02B 21/36* (2006.01)
*G02B 23/24* (2006.01)
*G03B 21/14* (2006.01)
*H04N 5/225* (2006.01)
*H04N 5/232* (2006.01)
*G02B 15/177* (2006.01)
*G03B 33/12* (2006.01)
*H04N 9/31* (2006.01)

(52) U.S. Cl.
CPC ...... *A61B 1/00112* (2013.01); *A61B 1/00188* (2013.01); *A61B 1/04* (2013.01); *G01J 1/08* (2013.01); *G02B 15/177* (2013.01); *G02B 21/241* (2013.01); *G02B 21/361* (2013.01); *G02B 23/2438* (2013.01); *G02B 23/2469* (2013.01); *G03B 21/142* (2013.01); *H04N 5/2254* (2013.01); *H04N 5/2256* (2013.01); *H04N 5/23293* (2013.01); *G03B 33/12* (2013.01); *H04N 9/3141* (2013.01); *H04N 2005/2255* (2013.01)

(56) References Cited

U.S. PATENT DOCUMENTS

| | | | |
|---|---|---|---|
| 8,749,893 | B2 | 6/2014 | Imaoka et al. |
| 8,767,321 | B2 | 7/2014 | Sunaga et al. |
| 8,947,793 | B2 * | 2/2015 | Morooka ............... G02B 15/14 359/684 |
| 9,116,286 | B2 | 8/2015 | Hayashi et al. |
| 2010/0202064 | A1 * | 8/2010 | Nagaoka ............... G02B 15/177 359/686 |
| 2012/0268831 | A1 * | 10/2012 | Yamanashi ........... G02B 15/177 359/686 |
| 2014/0340763 | A1 * | 11/2014 | Harada ................. G02B 15/177 359/680 |
| 2015/0103230 | A1 | 4/2015 | Morooka |

FOREIGN PATENT DOCUMENTS

| | | |
|---|---|---|
| JP | 2012242690 A | 12/2012 |
| JP | 2013037081 A | 2/2013 |
| JP | 2013088719 A | 5/2013 |
| JP | 5628090 B2 | 11/2014 |
| JP | 5631856 B2 | 11/2014 |

* cited by examiner

SA
FNO=1.24

AS
FIY = 10.14

DT
FIY = 10.14

CC
FIY = 10.14

SA
FNO=1.24

AS
FIY = 10.14

DT
FIY = 10.14

CC
FIY = 10.14

SA
FNO=1.23

AS
FIY = 10.14

DT
FIY = 10.14

CC
FIY = 10.14

486.13 —·—·—
656.27 - - - - -
587.56 ———

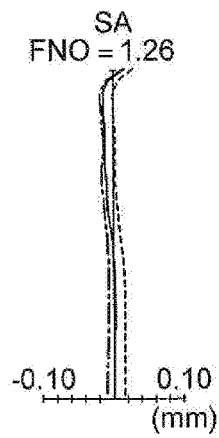
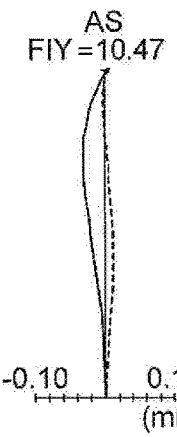
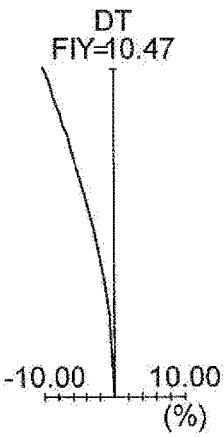
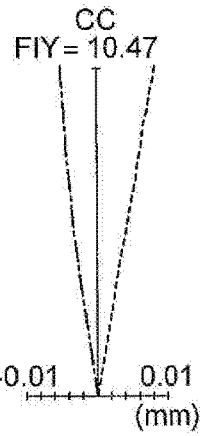
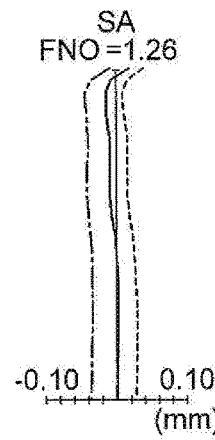
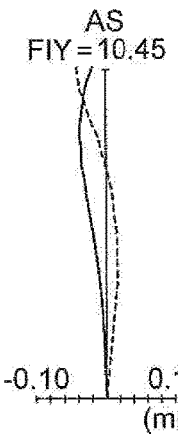
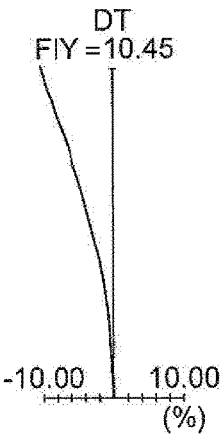
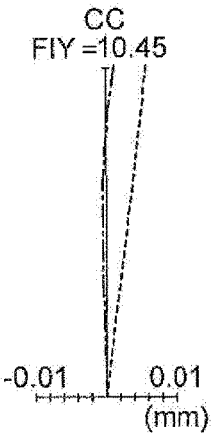
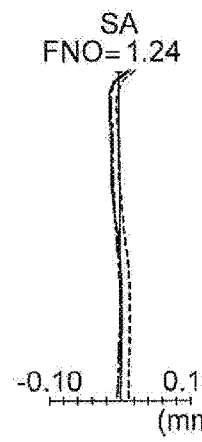
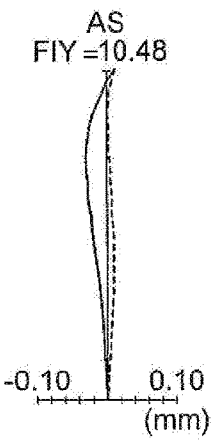
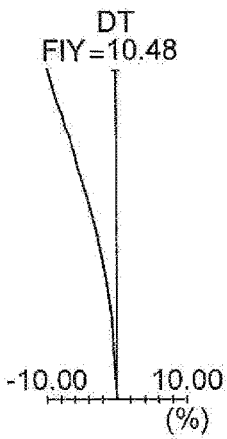
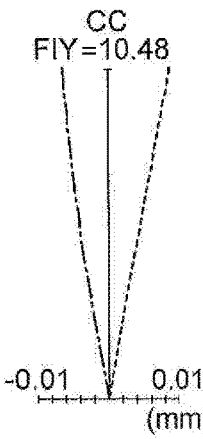

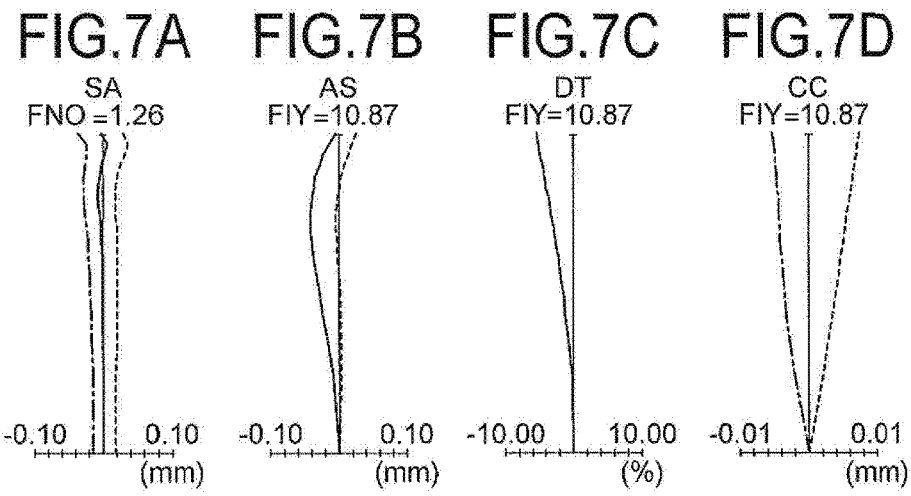

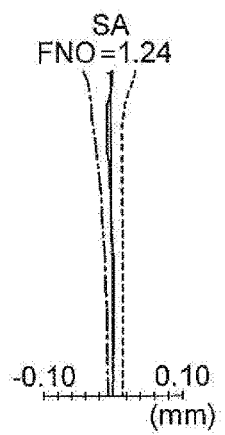
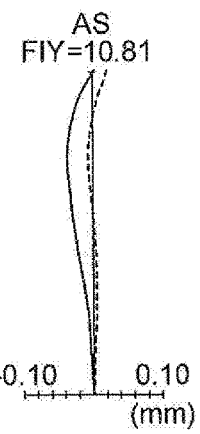
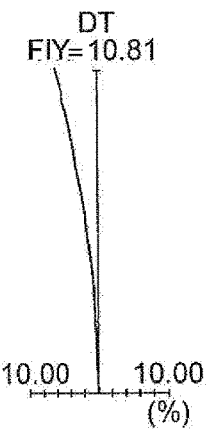
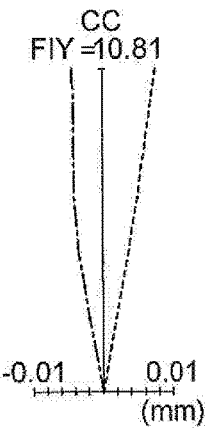
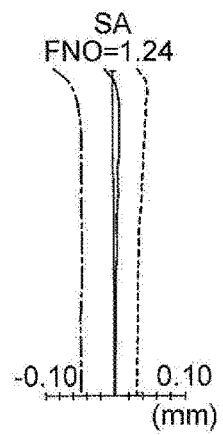
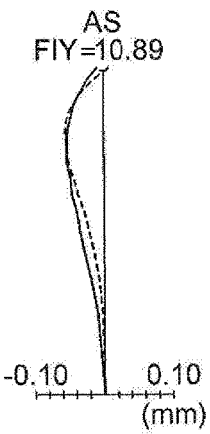
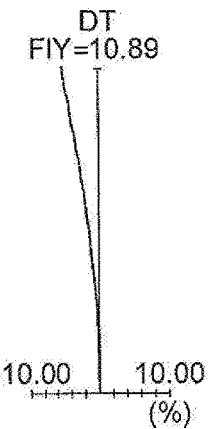
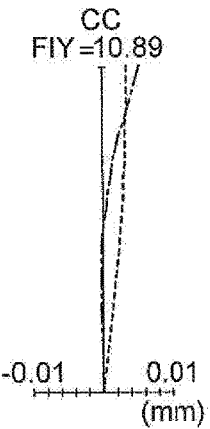
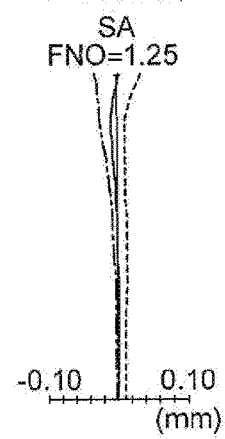
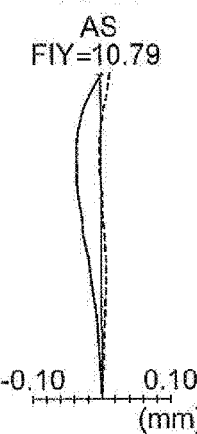
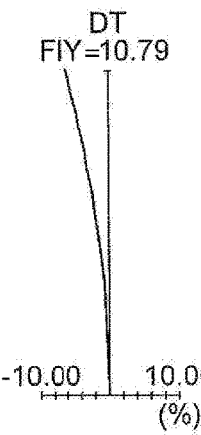
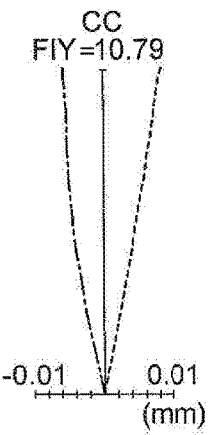

SINGLE FOCAL LENGTH LENS AND OPTICAL APPARATUS USING THE SAME

CROSS-REFERENCE TO RELATED APPLICATION

The present application is based upon and claims the benefit of priority from the prior Japanese Patent Application No. 2016-151091 filed on Aug. 1, 2016; the entire contents of which are incorporated herein by reference.

BACKGROUND OF THE INVENTION

Field of the Invention

The present invention relates to a single focal length lens and an optical apparatus using the same.

Description of the Related Art

Conventionally, a wide-angle lens and a standard lens have been used as a taking lens of a photographic camera and still video camera. As an optical system of the wide-angle lens and the standard lens, an optical system having a substantially symmetrical refractive power on two sides of an aperture stop has been proposed.

As a focusing method for these lenses, an inner focusing method is available. In the inner focusing method, focusing is carried out by moving some of the lenses on an image side of the aperture stop.

At the time of focusing, a lens or a lens unit moves. In a case of moving a lens, a lightweight lens is selected, and in a case of moving a lens unit, a lightweight lens unit with a comparatively fewer number of lenses is selected. Therefore, the inner focusing method has merits of increasing a focusing speed and reducing a cost.

In Japanese Patent Application Laid-open Publication No. 2012-220654, Japanese Patent Application Laid-open Publication No. 2012-226309, Japanese Patent No. 5628090 Publication, Japanese Patent Application Laid-open Publication No. 2012-242690, Japanese Patent Application Laid-open Publication No. 2013-037081, Japanese Patent Application Laid-open Publication No. 2013-088719, and Japanese Patent No. 5631856 Publication, taking lenses of an inner focusing type have been proposed. In the taking lenses disclosed in Japanese Patent Application Laid-open Publication No. 2012-220654 and Japanese Patent Application Laid-open Publication No. 2012-226309, an F-number is approximately 1.4 and an angle of view is not more than 50°. In taking lenses disclosed in Japanese Patent No. 5628090 Publication, Japanese Patent Application Laid-open Publication No. 2012-242690, and Japanese Patent Application Laid-open Publication No. 2013-088719, the F-number is approximately 1.8 and the angle of view is not more than 50°. In taking lenses disclosed in Japanese Patent Application Laid-open Publication No. 2013-037081 and Japanese Patent No. 5631856, the F-number is approximately 1.8 and the angle of view is not more than 60°.

SUMMARY OF THE INVENTION

A single focal length lens according to at least some of embodiments of the present invention comprises in order from an object side to an image side,
a first lens unit having a negative refractive power,
an aperture stop,
a second lens unit having a positive refractive power;
a third lens unit having a negative refractive power; and
a fourth lens unit having a positive refractive power, wherein
a position of the first lens unit, a position of the second lens unit, and a position of the fourth lens unit are fixed all the time, and
at the time of focusing from an object at infinity to an object at a short distance, the third lens unit moves toward the image side, and
the following conditional expressions (1), (2), and (3) are satisfied:

$$-5 < f1/f < -0.5 \quad (1),$$

$$-10 < f3/f < -1 \quad (2), \text{ and}$$

$$0.5 < f12/f < 1 \quad (3)$$

where,
f1 denotes a focal length of the first lens unit,
f denotes a focal length of an overall single focal length lens system at the time of focusing to an object at infinity,
f3 denotes a focal length of the third lens unit, and
f12 denotes a combined focal length of the first lens unit and the second lens unit.

Moreover, a single focal length lens according at least to some of the embodiments of the present invention comprises in order from an object side to an image side,
a first lens unit having a negative refractive power,
an aperture stop,
a second lens unit having a positive refractive power,
a third lens unit having a negative refractive power, and
a fourth lens unit having a positive refractive power, wherein
a position of the first lens unit, a position of the second lens unit, and a position of the fourth lens unit are fixed all the time, and
at the time of focusing from an object at infinity to an object at a short distance, the third lens unit moves toward the image side, and
the first lens unit includes an object-side sub lens unit and an image-side sub lens unit, and
an air lens having a biconvex shape is formed between the object-side sub lens unit and the image-side sub lens unit, and
the object-side sub lens unit has a negative refractive power, and includes at least two negative lenses nearest to the object, and
the image-side sub lens unit includes in order from the object side, at least one negative lens and at least one positive lens, and
the second lens unit includes in order from the object side, at least two positive lenses, at least one negative lens, and at least one positive lens, and
at least one of the positive lenses in the second lens unit satisfies the following conditional expression (4):

$$80 < vd2p \quad (4)$$

where,
vd2p denotes Abbe number for the positive lens in the second lens unit.

Moreover, an optical apparatus according to at least some of the embodiments of the present invention comprises,
the above-mentioned single focal length lens, and
an image pickup element which is disposed on an image side of the single focal length lens, wherein
the image pickup element has an image pickup surface, and converts an image formed on the image pickup surface by the single focal length lens to an electric signal.

An optical apparatus according to at least some of the embodiments of the present invention comprises, the above-mentioned single focal length lens, and a display element which is disposed on an image side of the single focal length lens, wherein the display element has a display surface, and an image displayed on the display surface is projected on an object side by the single focal length lens.

BRIEF DESCRIPTION OF THE DRAWINGS

FIG. 6A, FIG. 6B, FIG. 6C, FIG. 6D, FIG. 6E, FIG. 6F, FIG. 6G, FIG. 6H, FIG. 6I, FIG. 6J, FIG. 6K, and FIG. 6L (hereinafter, 'FIG. 6A to FIG. 6L') are aberration diagrams of a single focal length lens according to example 2;

FIG. 7A, FIG. 7B, FIG. 7C, FIG. 7D, FIG. 7E, FIG. 7F, FIG. 7G, FIG. 7H, FIG. 7I, FIG. 7J, FIG. 7K, and FIG. 7L (hereinafter, 'FIG. 7A to FIG. 7L') are aberration diagrams of a single focal length lens according to example 3;

FIG. 8A, FIG. 8B, FIG. 8C, FIG. 8D, FIG. 8E, FIG. 8F, FIG. 8G, FIG. 8H, FIG. 8I, FIG. 8J, FIG. 8K, and FIG. 8L (hereinafter, 'FIG. 8A to FIG. 8L') are aberration diagrams of a single focal length lens according to example 4;

DETAILED DESCRIPTION OF THE INVENTION

Figure 1:
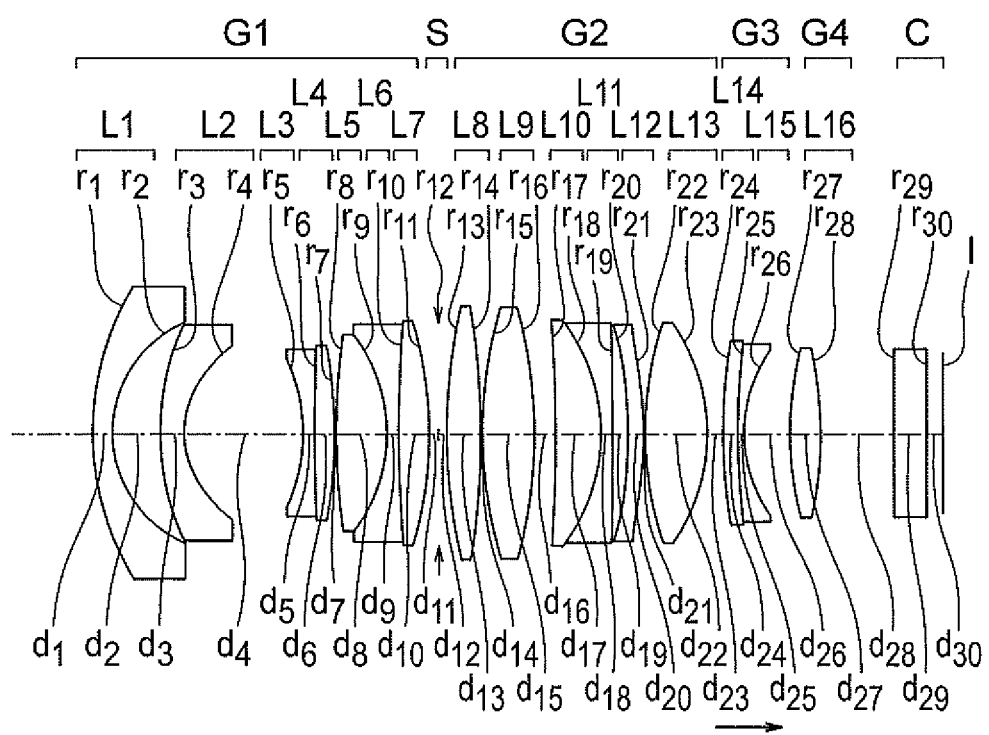
FIG. 1 is a lens cross-sectional view of a single focal length lens according to an example 1 at the time of focusing to an object at infinity.
Figure 2:
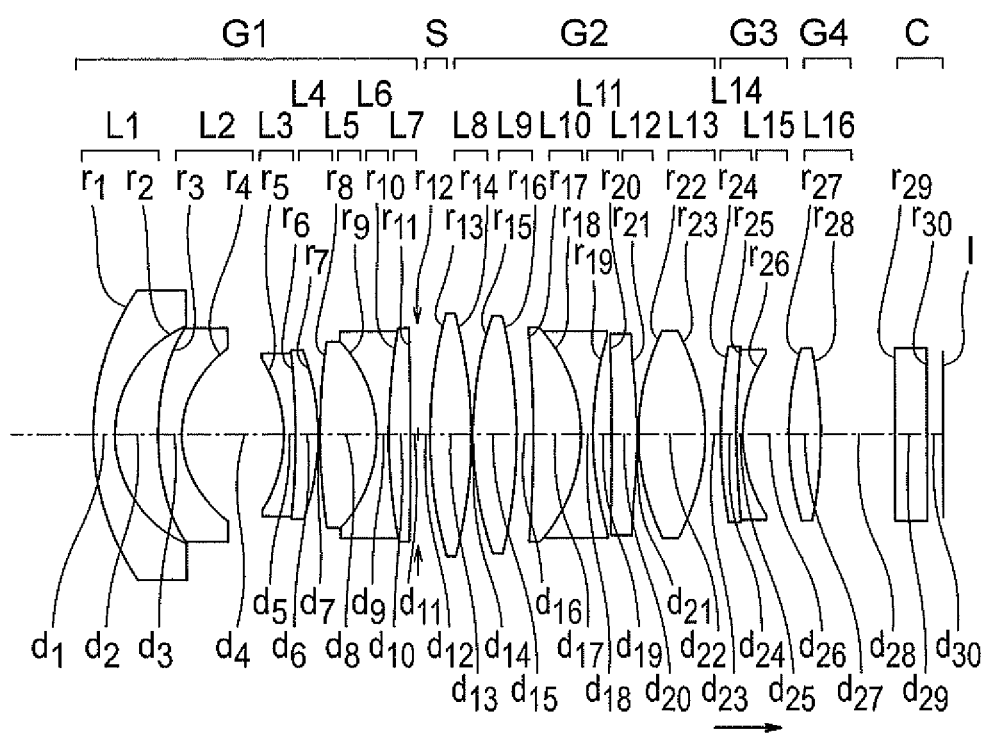
FIG. 2 is a lens cross-sectional view of a single focal length lens according to an example 2 at the time of focusing to an object at infinity.
Figure 3:
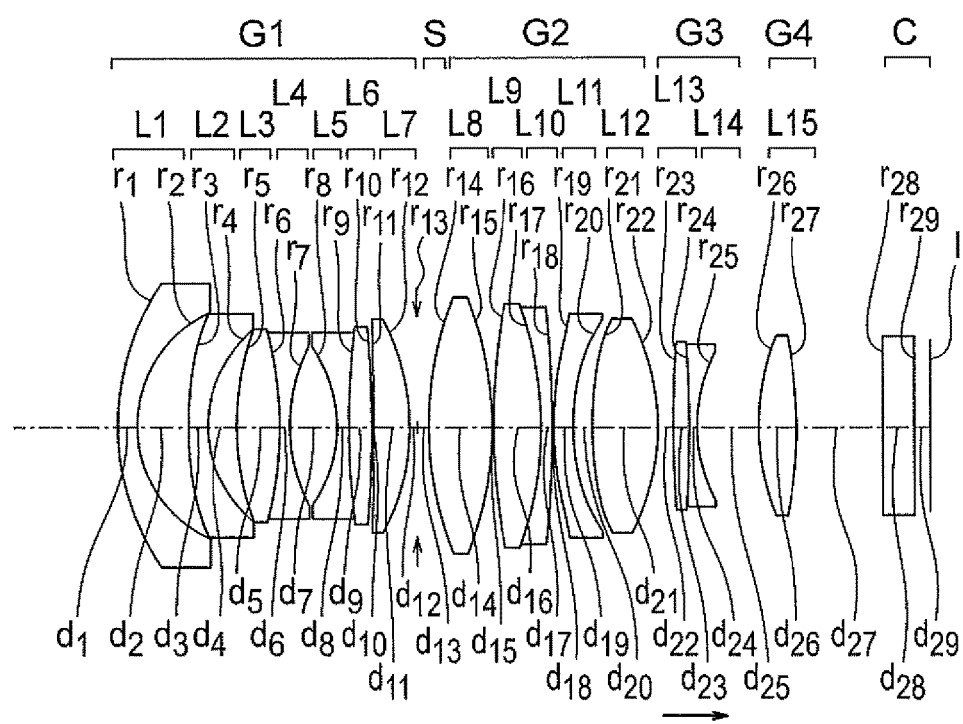
FIG. 3 is a lens cross-sectional view of a single focal length lens according to an example 3 at the time of focusing to an object at infinity.
Figure 4:
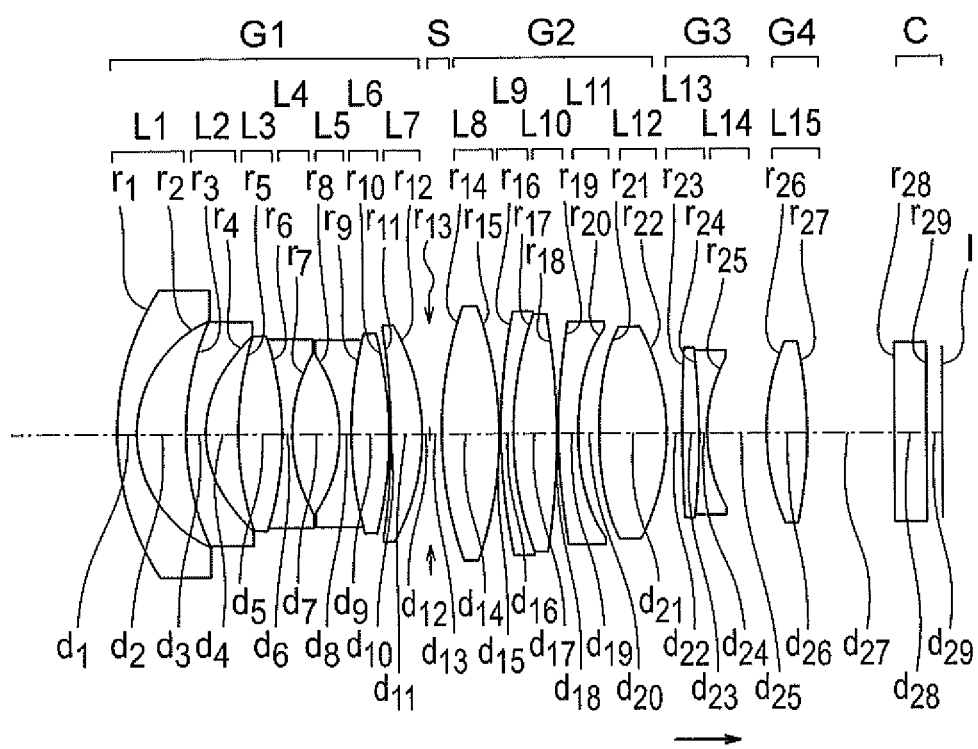
FIG. 4 is a lens cross-sectional view of a single focal length lens according to an example 4 at the time of focusing to an object at infinity.
Figure 5A:
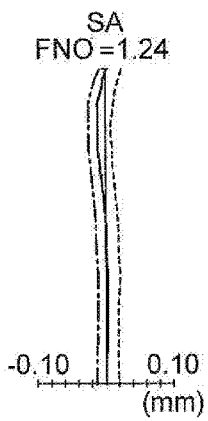
FIG. 5A, FIG. 5B, FIG. 5C, FIG. 5D, FIG. 5E, FIG. 5F, FIG. 5G, FIG. 5H, FIG. 5I, FIG. 5J, FIG. 5K, and FIG. 5L (hereinafter, 'FIG. 5A to FIG. 5L') are aberration diagrams of a single focal length lens according to example 1.
Figure 5B:
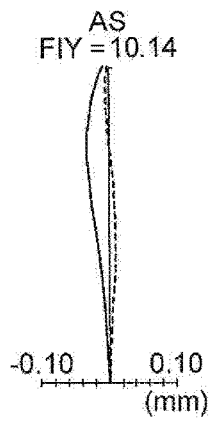
Figure 5C:
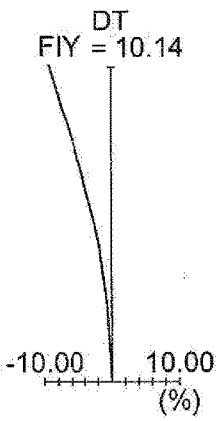
Figure 5D:
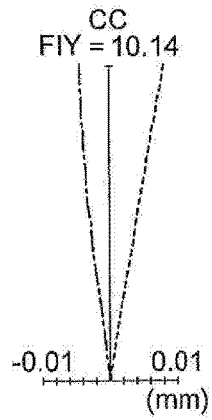
Figure 5E:
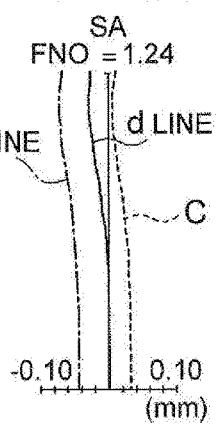
Figure 5F:
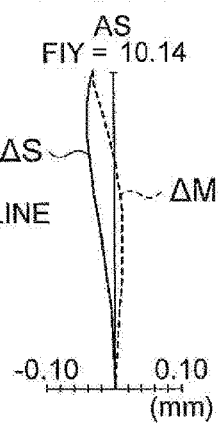
Figure 5G:
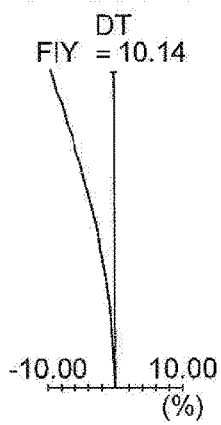
Figure 5H:
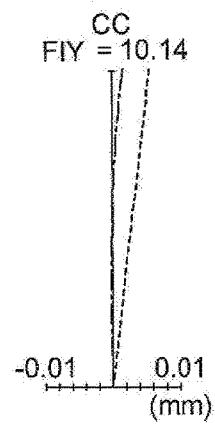
Figure 5I:
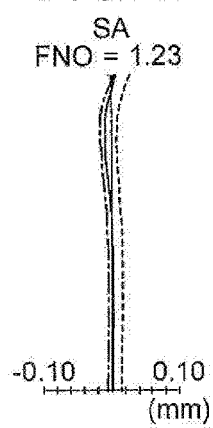
Figure 5J:
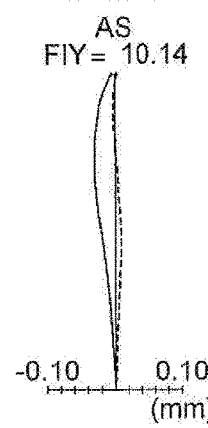
Figure 5K:
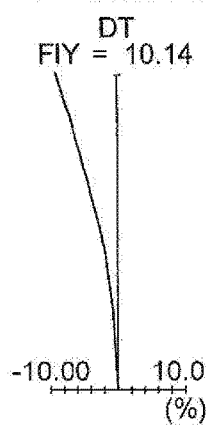
Figure 5L:
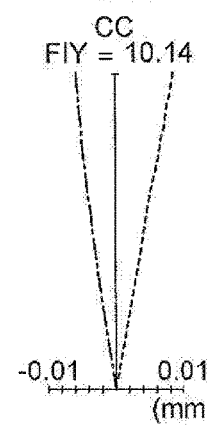

Prior to the explanation of examples, action and effect of embodiments according to certain aspects of the present invention will be described below. In the explanation of the action and effect of the embodiments concretely, the explanation will be made by citing concrete examples. However, similar to a case of the examples to be described later, aspects exemplified thereof are only some of the aspects included in the present invention, and there exists a large number of variations in these aspects. Consequently, the present invention is not restricted to the aspects that will be exemplified.

A basic arrangement of a single focal length lens of the present embodiment (hereinafter, referred to as 'basic arrangement of the present embodiment') will be described below. In the basic arrangement of the present embodiment, the single focal length lens includes in order from an object side to an image side, a first lens unit having a negative refractive power, an aperture stop, a second lens unit having a positive refractive power, a third lens unit having a negative refractive power, and a fourth lens unit having a positive refractive power, wherein a position of the first lens unit, a position of the second lens unit, and a position of the fourth lens unit are fixed all the time, and at a time of focusing from an object at infinity to an object at a short distance, the third lens unit moves toward the image side.

In the basic arrangement of the present embodiment, the single focal length lens has in order from the object side to the image side, the first lens unit having a negative refractive power, the aperture stop, and the second lens unit having a positive refractive power. By having such arrangement, it is possible to widen an angle of view easily.

In the basic arrangement of the present embodiment, the third lens unit having a negative refractive power is disposed on the image side of the second lens unit. By making such arrangement, it is possible to secure an appropriate back focus comparatively easily.

Moreover, by making the third lens unit to be moved toward the image side, the focusing is carried out from an object at infinity to an object at a short distance.

In a case of making the negative refractive power of the third lens unit large in order to make a magnification of photographing large at a time of focusing to an object at a short distance (hereinafter, referred to as 'near point magnification'), since the back focus becomes large, an overall length of an optical system becomes long.

Moreover, when the refractive power of the third lens unit is made weak, an amount of movement of the third lens unit becomes large. Particularly, at a time of focusing to an object at a short distance, a variation in a spherical aberration and a variation in a curvature of field become large. Therefore, the refractive power of the third lens unit cannot be made that small.

In the basic arrangement of the present embodiment, the fourth lens unit having a positive refractive power is disposed on the image side of the third lens unit. In this case, it is possible to let the magnification ratio of the overall system to be shared by the third lens unit and the fourth lens unit.

Moreover, by making such arrangement, it is possible to make the refractive power of the third lens unit which is a focusing unit large or in other words, to make the load of magnification ratio on the third lens unit large. Therefore, even when the magnification ratio for a short distance is made large, the amount of movement for focusing from infinity to an object at a short distance becomes small. As a result, it is possible to suppress an aberration variation due to the movement of the third lens unit.

Moreover, by disposing the fourth lens unit having a positive refractive power, even when the negative refractive power of the third lens unit is made large, the back focus does not become large. Therefore, disposing the fourth lens unit is advantageous for shortening the overall length of the optical system.

Particularly, in an optical system in which an aperture is made large, at a time of focusing to an object at a short distance, the spherical aberration and the curvature of field are susceptible to become large. However, in the basic arrangement of the present embodiment, it is not necessary to make the refractive power of the third lens unit small. Consequently, it is possible to make small the spherical aberration and the curvature of field at the time of focusing to an object at a short distance.

Moreover, since it is not necessary to make the refractive power the third lens unit small, the amount of movement of the third lens unit does not increase. Therefore, the overall length of the optical system also does not become long.

Moreover, by disposing the fourth lens unit on the image side of the third lens unit, it is possible to make Petzval sum small as well as to correct a chromatic aberration favorably.

A single focal length lens according to a first embodiment has the abovementioned basic arrangement, and the following conditional expressions (1), (2), and (3) are satisfied:

$$-5 < f1/f < -0.5 \quad (1),$$

$$-10 < f3/f < -1 \quad (2), \text{ and}$$

$$0.5 < f12/f < 1 \quad (3)$$

where, f1 denotes a focal length of the first lens unit, f denotes a focal length of an overall single focal length lens system at the time of focusing to an object at infinity, f3 denotes a focal length of the third lens unit, and f12 denotes a combined focal length of the first lens unit and the second lens unit.

In conditional expression (1), the focal length of the first lens unit is regulated. In conditional expression (2), the focal length of the third lens unit is regulated. Satisfying conditional expressions (1) and (2) is advantageous for small-sizing of the optical system when the aperture is made large, and for reduction of aberration variation at the time of focusing to an object at a short distance.

By making so as not to below a lower limit value of conditional expression (1), it is possible to secure adequately the negative refractive power of the first lens unit. As a result, it becomes easy to secure a wide angle of view. Moreover, not falling below the lower limit value of conditional expression (1) is advantageous for small-sizing of the first lens unit.

By making so as not to exceed an upper limit value of conditional expression (1), it is possible to suppress an increase in the negative refractive power of the first lens unit. As a result, an increase in a lateral magnification of a plurality of lens units (hereinafter, referred to as 'lens unit A') disposed on the image side of the first lens unit is relatively suppressed.

An aberration occurred in the first lens unit is enlarged in the lens unit A. The lens unit A includes the third lens unit. Since the third lens unit moves at the time of focusing, the aberration varies with the movement of the third lens unit. By suppressing the increase in the lateral magnification of the lens unit A, it becomes easy to suppress the variation in aberration, and particularly, variation in the curvature of field and variation in the coma, at a time of focusing to an object at a short distance.

Moreover, by suppressing the increase in the negative refractive power of the first lens unit, it becomes easy to suppress an increase in a diameter of an axial light beam incident on the second lens unit. Not exceeding the upper limit value of conditional expression (1) is advantageous for small-sizing of the second lens unit.

By making so as not to fall below a lower limit value of conditional expression (2), it is possible to secure adequately the negative refractive power in the third lens unit. As a result, it is possible to suppress an increase in the amount of movement of the third lens unit at the time of focusing. Making so as not to fall below the lower limit value of conditional expression (2) is advantageous for small-sizing of the single focal length lens.

Moreover, it is easy to make Petzval sum small. Consequently, making so as not to fall below the lower limit value of conditional expression (2) is advantageous for correction of the curvature of field and correction of the chromatic aberration.

By making so as not to exceed an upper limit value of conditional expression (2), it is possible to suppress the increase in the negative refractive power in the third lens unit. As a result, it is possible to correct favorably various aberrations, particularly the spherical aberration and the coma, at a time of focusing to an object at a short distance, in the overall single focal length lens system. Making so as not to exceed the upper limit value of conditional expression (2) is advantageous for correction of the abovementioned aberrations.

In conditional expression (3), the combined focal length of the first lens unit and the second lens unit is regulated. By satisfying conditional expression (3), it is possible to divide the load of aberration correction between the third lens unit and the fourth lens unit appropriately. Satisfying conditional expression (3) is advantageous for small-sizing of the overall single focal length lens system and aberration reduction of the overall single focal length lens system.

An aberration that occurs in a lens unit including the first lens unit and the second lens unit (hereinafter, referred to as 'combined lens unit') is enlarged in a plurality of lens units disposed on the image side of the second lens unit (hereinafter, referred to as 'lens unit B').

By making so as not to fall below a lower limit value of conditional expression (3), a focal length of the combined lens unit does not become excessively shorter than the focal length of the overall single focal length lens system. In this case, an increase in magnification in the lens unit B is suppressed. As mentioned above, the aberration occurred in the combined lens unit is enlarged in the lens unit B, but the aberration after the enlargement does not become that large.

This signifies that it is possible to make large an amount of acceptable aberration that occurs in the combined lens unit. Consequently, it is possible to reduce the number of lenses in the first lens unit and the number of lenses in the second lens unit. Thus, making so as not to fall below the lower limit value of conditional expression (3) is advantageous for small-sizing of the optical system and making it low cost.

By making so as not to exceed an upper limit value of conditional expression (3), the focal length of the combined lens unit does not become excessively longer than the focal length of the overall single focal length lens system. In this case, the magnification in the lens unit B is suppressed from becoming excessively small. As the magnification in the lens unit B becomes small, since an aberration that occurs in the combined lens unit is required to be reduced in the lens unit B, a load of aberration correction becomes substantial. However, by making so as not to exceed the upper limit value, it is possible to suppress an increase in the load of aberration correction on the lens unit B.

Specifically, it is possible to suppress an increase in the load of aberration correction on the third lens unit and on the fourth lens unit. Since the third lens unit moves at the time of focusing, the aberration varies with the movement of the third lens unit. As an increase in the load of aberration correction on the lens unit B can be suppressed, it is possible to use the performance of aberration correction in the lens unit B for suppressing the variation in aberration at a time of focusing to a near object. As a result, it is possible to reduce the variation in aberration, particularly, the variation in the curvature of field and the variation in the coma, at the time of focusing to the near object.

Moreover, since it is possible to suppress a decentering sensitivity in the third lens unit and a decentering sensitivity in the fourth lens unit, manufacturing of a single focal length lens becomes easy. The decentering sensitivity can be expressed by a degree of degradation of an image with respect to an amount of shift of a lens or a lens unit from a designed value.

According to the single focal length lens of the first embodiment, it is possible to realize a single focal length lens in which both the small F-number and wide angle of view are secured. More specifically, it is possible to realize a single focal length lens of inner focusing type with the F-number of 1.4 and the angle of view not less than 60°.

In the single focal length lens of the first embodiment, it is preferable that the first lens unit include an object-side sub lens unit and an image-side sub lens unit, and an air lens having a biconvex shape be formed between the object-side sub lens unit and the image-side sub lens unit, and the object-side sub lens unit have a negative refractive power, and include at least two negative lenses nearest to object, and the image-side sub lens unit include in order from the object side, at least one negative lens and at least one positive lens.

In the first lens unit, the air lens having a biconvex shape is formed between the object-side sub lens unit and the image-side sub lens unit. By making such arrangement, it is possible to correct favorably the spherical aberration and the astigmatism when an aperture is made large.

The object-side sub lens unit is disposed on the object side of the air lens having a biconvex shape. The object-side sub lens unit includes at least to negative lenses nearest to object. By having such arrangement, even when the angle of view is made wide and the aperture is made large, it becomes easy to carry out a favorable correction of an off-axis aberration.

The image-side sub lens unit is disposed on the image side of the air lens having a biconvex shape. The image-side sub lens unit includes in order from the object side, at least one negative lens and at least one positive lens. By having such arrangement, it is possible to carry out favorably the correction of the spherical aberration and correction of the chromatic aberration.

In the object-side sub lens unit, it is possible to let at least two negative lenses to be meniscus lenses having a convex surface directed toward the object side. Making such arrangement is advantageous for correction of the coma.

In the single focal length lens of the first embodiment, it is preferable that the second lens unit include in order from the object side, a first sub lens unit, a second sub lens unit, and a third sub lens unit, and the first sub lens unit have a positive refractive power, and include at least two positive lenses, and the second sub lens unit have a negative refractive power, and include at least one negative lens, and the third sub lens unit have a positive refractive power, and include at least one positive lens, and at least one of the positive lenses in the second lens unit satisfy the following conditional expression (4):

$$80 < vd2p \quad (4)$$

where, vd2p denotes Abbe number for the positive lens in the second lens unit.

In the second lens unit, the first sub lens unit is disposed at a position nearest to the first lens unit. The first sub lens unit has a positive refractive power, and includes at least two positive lenses. By having such arrangement, it is possible to lower a light height at the first lens unit, and to correct favorably the spherical aberration which is susceptible to occur by making the aperture large.

The second sub lens unit is disposed on the image side of the first sub lens unit. The second sub lens unit has a negative refractive power, and includes at least one negative lens. The third sub lens unit is disposed on the image side of the second sub lens unit. The third lens unit has a positive refractive power, and includes at least one positive lens.

In this case, since the second sub lens unit has a negative refractive power and the third sub lens unit has a positive refractive power, it is possible to arrange an optical system of a retro-focus type by the second sub lens unit and the third sub lens unit. In this case, it is possible to let a position of a principal point in the second lens unit to be toward an image plane. As a result of this, it is possible to secure a back focus adequately. Moreover, it is possible to lower a height of an off-axis light ray incident on the third lens unit.

Moreover, it is preferable that at least one of the positive lenses in the second lens unit satisfy conditional expression (4). Conditional expression (4) is an expression that regulates appropriately Abbe number for the positive lens in the second lens unit.

The second lens unit is disposed on the image side of the first lens unit. Since the first lens unit has a negative refractive power, a height of an axial marginal ray is susceptible to be the maximum at the second lens unit. In this case, by using a material with a low dispersion for any one the positive lenses in the second lens unit, it is possible to correct favorably a longitudinal chromatic aberration of the overall single focal length lens system. Satisfying conditional expression (4) is advantageous for correction of the longitudinal chromatic aberration when the aperture is made large.

Satisfying conditional expression is particularly effective when the F-number of single focal length lens is to be made not more than 1.4.

In the second lens unit, for achieving both small-sizing and making the aperture large, it is preferable to make a refractive power large. However, when the refractive power is made large, the spherical aberration and the coma are susceptible to increase. In this case, it is preferable to use an aspheric surface for at least one of the lens units that form the optical system of the retro-focus type. By making such arrangement, it is possible to reduce the spherical aberration and the coma appropriately even when the small-sizing is carried out and the aperture is made large.

The lens units that form the optical system of retro-focus type are the second sub lens unit and the third sub lens unit. Therefore, it is preferable to use an aspheric surface for at least the second sub lens unit or the third sub lens unit. The number of aspheric surfaces may be one or in plurality.

In the single focal length lens of the first embodiment, it is preferable that the following conditional expression (5) be satisfied:

$$0.05 < Dm/St < 1 \quad (5)$$

where,

Dm denotes a maximum variable air space from among variable air spaces in the single focal length lens, and St denotes a maximum diameter of the aperture stop.

In conditional expression (5), the variable space is regulated appropriately. Satisfying conditional expression (5) is advantageous for making an aperture large, small-sizing, and aberration correction.

By making so as not to fall below a lower limit value of conditional expression (5), it is possible to secure the variable air space adequately. In this case, it becomes easy to suppress an increase in the refractive power of a lens unit that is to be moved at the time of focusing. Making so as not to fall below the lower limit value of conditional expression (5) is advantageous for reduction of aberration in the overall single focal length lens system when the aperture is made large.

By making so as not to exceed an upper limit value of conditional expression (5), it is possible to make the variable air space smaller than a diameter of the aperture stop. As a result, it is possible to make the aperture large and to carry out small-sizing.

In the single focal length lens of the first embodiment, it is preferable that the following conditional expression (6) be satisfied:

$$0.2<DA/DL<1 \quad (6)$$

where,

DA denotes a sum of air spaces between a lens surface nearest to the object of the single focal length lens and a lens surface nearest to an image of the single focal length lens, and DL denotes a sum of lens thicknesses between the lens surface nearest to the object of the single focal length lens and the lens surface nearest to the image of the single focal length lens.

In conditional expression (6), the sum of the air spaces in the overall single focal length lens system is regulated. Satisfying conditional expression (6) is advantageous for aberration correction of the overall single focal length lens system when the aperture is made large.

By making so as not to fall below a lower limit value of conditional expression (6), it is possible to secure the sum of air spaces with respect to a sum of lens thicknesses of the overall single focal length lens system. Making an arrangement so as not to fall below the lower limit value of conditional expression (6) is advantageous for making a radius of curvature of a lens to be small easily and for securing a refractive power of each lens.

By making so as not to exceed an upper limit value of conditional expression (6), it is possible not to let the sum of the air spaces with respect to the sum of the lens thicknesses of the overall single focal length lens system to be excessively large. In this case, it is possible to secure adequately the number of lenses relatively. Making so as not to exceed the upper limit value of conditional expression (6) is advantageous for aberration correction of the overall single focal length lens system when the aperture is made large.

In the single focal length lens of the first embodiment, it is preferable that the following conditional expressions (7) and (8) be satisfied:

$$60°<2\omega<190° \quad (7), and$$

$$0.8<FNOm<1.4 \quad (8)$$

where,

ω denotes a half angle of view at the time of focusing to an object at infinity, and FNOm denotes a minimum, F-number at the time of focusing to an object at infinity.

By satisfying conditional expressions (7) and (8), it is possible to widen the angle of view while suppressing the aperture of the lens positioned nearest to object from becoming excessively large. For aberration correction, although it is necessary to increase the number of lenses and to make the aperture large, it is possible to secure brightness of the optical system while suppressing the increase in the number of lenses and the enlargement of the aperture from becoming excessive. Accordingly, it becomes easy to carry out small-sizing while securing the angle of view and brightness advantageous for snap photography.

A single focal length lens according to a second embodiment has the abovementioned basic arrangement and the first lens unit includes an object-side sub lens unit and an image-side sub lens unit, and an air lens having a biconvex shape is formed between the object-side sub lens unit and the image-side sub lens unit, and the object-side sub lens unit has a negative refractive power, and includes at least two negative lenses nearest to an object, and the image-side sub lens unit includes in order from the object side, at least one negative lens and at least one positive lens, and the second lens unit includes in order from the object side, at least two positive lenses, at least one negative lens, and at least one positive lens, and at least one of the positive lenses in the second lens unit satisfies conditional expression (4).

The single focal length lens according to the second embodiment includes in order from an object side, the first lens unit, an aperture stop, and the second lens unit having a positive refractive power. In the first lens unit, the air lens having a biconvex shape is formed between the object-side sub lens unit and the image-side sub lens unit, and the second lens unit includes in order from the object side, at least two positive lenses, at least one negative lens, and at least one positive lens.

In the single focal length lens according to the second embodiment, an optical system of Gaussian type is formed by the lenses in the first lens unit, the aperture stop, and the lenses in the second lens unit. By making such arrangement, an arrangement of an optical system is such that it is easy to make an aperture large.

Moreover, by making such arrangement, the aberration correction of the overall optical system can be mainly carried out in lens units positioned on the object side of the third lens unit, or in other words, the lens units that form the optical system of Gaussian type. Therefore, since it is possible to make small the load of aberration correction on the third lens unit, the third lens unit can be let to include at least one negative lens. The third lens unit moves as the focusing lens unit at the time of focusing. Consequently, making such arrangement is advantageous for making the focusing lens unit light-weight.

In the first lens unit, the air lens having a biconvex shape is formed between the object-side sub lens unit and the image side sub lens unit. In this case, it is preferable to make an arrangement such that the object-side sub lens unit and the image-side sub lens unit are symmetrical about the air lens having a biconvex shape. By making such arrangement, it is possible to let an arrangement of the first lens unit to be an arrangement of an optical system of Gaussian type. As a result, it is possible to correct favorably the spherical aberration and the astigmatism when the aperture is made large.

The object-side sub lens unit is disposed on the object side of the air lens having a biconvex shape. In the object-side sub lens unit, at least two negative lenses are disposed nearest to object. By making such arrangement, correction of an off-axis aberration can be carried out favorably when the aperture is made large.

The image-side sub lens unit is disposed on the image side of the air lens having a biconvex shape. The image-side sub lens unit includes in order from the object side, at least one negative lens and at least one positive lens. By making such arrangement, it is possible to secure symmetry of the Gaussian type, and moreover, to carry out favorably the correction of the spherical aberration and the chromatic aberration.

In the object-side sub lens unit, it is possible to let the negative lens to be a meniscus lens having a convex surface directed toward the object side. By making such arrangement, it is possible to carry out the correction of the coma.

In the second lens unit, at least two positive lenses are disposed on the object side. By making such arrangement, it is possible to lower a height of a light ray incident from the first lens unit and to correct favorably the spherical aberration that occurs because of making the aperture large.

At least one negative lens and at least one positive lens are disposed on the image side of at least two positive lenses. By making such arrangement, it is possible to form an optical system of a retro-focus type. In this case, it is possible to let a position of a principal point in the second lens unit toward an image plane. As a result, it is possible to secure the back focus adequately. Moreover, it is possible to lower a height of an off-axis light ray incident on the third lens unit.

It is preferable that at least one of the positive lenses in the second lens unit satisfy conditional expression (4). A technical significance of conditional expression (4) is as mentioned above.

In a case of making the F-number of a single focal length lens not more than 1.4, or in other words, letting the optical system have a large aperture, it is desirable to use a glass material that satisfies conditional expression (4) for at least one of the positive lenses.

In the second lens unit, for achieving both small-sizing and making the aperture large, it is necessary to make a refractive power of the positive lens relatively larger. However, when the refractive power is made large, the spherical aberration and the coma are susceptible to increase. In this case, it is preferable to use an aspheric surface for at least one of the lenses that form the optical system of the retro-focus type. By making such arrangement, it is possible to correct the spherical aberration and the coma appropriately even when the small-sizing is carried out and the aperture is made large.

The lenses that form the optical system of retro-focus type are at least one positive lens and at least one negative lens. Therefore, it is preferable to use an aspheric surface for at least one of these lenses. The number of aspheric surfaces may be one or in plurality.

In the single focal length lens of the second embodiment, it is preferable that the following conditional expression (3) be satisfied:

$$0.5 < f12/f < 1 \quad (3)$$

where, f12 denotes the combined focal length of the first lens unit and the second lens unit, and f denotes the focal length of an overall single focal length lens system at the time of focusing to an object at infinity.

A technical significance of conditional expression (3) is as mentioned above.

In a case of falling below the lower limit value of conditional expression (3), the focal length of the combined lens unit becomes excessively shorter than the focal length of the overall single focal length lens system. In this case, an aberration that occurs in the combined lens system increases. The aberration occurred in the combined lens unit is enlarged in the lens unit B. Therefore, it is necessary to correct the aberration occurring in the combined lens unit to be small to some extent.

However, for correcting favorably the aberration that occurs in the combined lens unit, it is necessary to increase the number of lenses. As the number of lenses increases, the size of the optical system becomes large and there is a rise in the cost. Thus, falling below the lower limit value of conditional expression (3) is contrary to making the optical system small-sized and low cost.

In a case of exceeding the upper limit value of conditional expression (3), the focal length of the combined lens system becomes excessively longer than the focal length of the overall single focal length lens system. In this case, as the focal length of the combined lens system becomes long, the magnification in the lens unit B becomes excessively small, and since it is necessary to reduce the aberration occurred in combined lens unit, in the lens unit B, it is necessary to make the aberration occurring in the lens unit B to be small to some extent.

The lens unit B includes the third lens unit and the fourth lens unit. When an attempt is made to make the aberration in the lens unit B to be small to some extent, the load of aberration correction increases on the third lens unit and on the fourth lens unit.

Since the third lens unit moves at the time of focusing, the aberration varies with the movement of the third lens unit. As the load of aberration correction on the lens unit B increases, it becomes difficult to use the performance of aberration correction in the lens unit B for suppressing the variation in aberration at a time of focusing to the near object. As a result, the variation in aberration, particularly the variation in the curvature of field and the variation in the coma, at the time of focusing to the near object become large. Therefore, it is not preferable to exceed the upper limit value of conditional expression (3).

Moreover, the sensitivity of manufacturing error due to decentering becomes high in the third lens unit and in the fourth lens unit. For this reason, exceeding the upper limit value of conditional expression (3) is not preferable from manufacturing point of view.

In the single focal length lens of the second embodiment, it is preferable that the following conditional expression (5) be satisfied:

$$0.05 < Dm/St < 1 \quad (5)$$

where,

Dm denotes the maximum variable air space from among variable air spaces in the single focal length lens, and St denotes the maximum diameter of the aperture stop.

A technical significance of conditional expression (5) is as mentioned above.

By satisfying conditional expression (5), even when the aperture is made large, it is possible to make the imaging performance in the overall single focal length lens system favorable without letting the optical system to be large-sized.

In a case of falling below a lower limit value of conditional expression (5), it is advantageous for small-sizing of the optical system. However, for shortening the variable air space, it is necessary to make the refractive power of each lens large. For this reason, it becomes difficult to correct favorably an aberration of the overall single focal length lens system when the aperture is made large.

In a case of exceeding an upper limit value of conditional expression (5), the variable space becomes larger than the diameter of the aperture stop. Therefore, when the aperture is made large, small-sizing of the optical system becomes difficult.

In the single focal length lens of the second embodiment, it is preferable that the following conditional expression (6) be satisfied:

$$0.2<DA/DL<1 \quad (6)$$

where,

DA denotes the sum of air spaces between a lens surface nearest to an object of the single focal length lens and a lens surface nearest to an image of the single focal length lens, and DL denotes the sum of lens thicknesses between the lens surface nearest to the object of the single focal length lens and the lens surface nearest to the image of the single focal length lens.

A technical significance of conditional expression (6) is as mentioned above.

By satisfying conditional expression (6), it is possible to correct favorably the aberration of the overall single focal length lens system when the aperture is made large.

In a case of falling below a lower limit value of conditional expression (6), the sum of the air spaces with respect to the sum of the lens thicknesses of the overall single focal length lens system becomes small. Therefore, it is necessary to make the refractive power of each lens large, after making the radius of curvature of each lens large. In that case, since it is necessary to increase the number of lenses for the aberration correction when the aperture is made large, the lens cost increases. Therefore, failing below the lower limit value of conditional expression (6) is not preferable.

In a case of exceeding an upper limit value of conditional expression (6), the sum of the air spaces with respect to the sum of the lens thicknesses of the overall single focal length lens system becomes large. Therefore, it is not possible to increase the number of lenses relatively. As a result, it becomes difficult to correct favorably the aberration of the single focal length lens system when the aperture is made large.

In the single focal length lens of the second embodiment, it is preferable that the following conditional expressions (7) and (8) be satisfied:

$$60°<2\omega<190° \quad (7), \text{ and}$$

$$0.8<FNOm<1.4 \quad (8)$$

where,

ω denotes the half angle of view at the time of focusing to an object at infinity, and FNOm denotes the minimum F-number at the time of focusing to an object at infinity.

A technical significance of conditional expression (6) and a technical significance of conditional expression (7) are as mentioned above.

An optical apparatus of the present embodiment includes the abovementioned single focal length lens, and an image pickup element which is disposed on an image side of the single focal length lens, wherein the image pickup element has an image pickup surface, and converts an image formed on the image pickup surface by the single focal length lens to an electric signal.

According to the optical apparatus of the present embodiment, it is possible to capture a wide photographic range, with a low noise and high resolution.

The optical apparatus of the present embodiment includes the abovementioned single focal length lens, and a display element which is disposed on an image side of the single focal length lens, wherein the display element has a display surface, and an image displayed on the display surface is projected on an object side by the single focal length lens.

According to the optical apparatus of the present embodiment, it is possible to project an image with a low noise and high resolution over a wide projection range.

Moreover, it is preferable that the optical apparatus of the present embodiment includes an image converting unit, and the image converting unit converts an electric signal including a distortion by the single focal length lens to an image signal in which the distortion has been corrected by image processing.

When the single focal length lens has a distortion, an optical image also has a distortion. When such optical image is captured by an image pickup element, the electric signal subjected to conversion by the image pickup element includes distortion. Therefore, it is preferable to convert the electric signal including distortion to an image signal in which the distortion has been corrected by image processing, by using the image converting unit (image processing unit).

By converting the distortion electrically, it is possible to reduce a load of aberration correction of the single focal length lens. Moreover, it becomes easy to secure an appropriately large negative refractive power for the first lens unit. For such reason, the electrical correction of distortion is advantageous for small-sizing and achieving a high zooming ratio of the optical system. Moreover, by changing an amount of correction of distortion for each color signal, the chromatic aberration of magnification may also be corrected by image processing.

For each conditional expression, the upper limit value or the lower limit value may be changed as follows. It is preferable to change the upper limit value or the lower limit value as it enables to achieve more assured effect of each conditional expression.

For conditional expression (1), it is more preferable to let the lower limit value to be −3.5, and −2.5 is even more preferable.

Moreover, for conditional expression (1), it is more preferable to let the upper limit value to be −0.8, and −1 is even more preferable.

For conditional expression (2), it is more preferable to let the lower limit value to be −6, and −4 is even more preferable.

Moreover, for conditional expression (2), it is more preferable to let the upper limit value to be −1.5, −2 is even more preferable.

For conditional expression (3), it is more preferable to let the lower limit value to be 0.65, and 0.75 is even more preferable.

Moreover, for conditional expression (3), it is more preferable to let the upper limit value to be 0.97, and 0.95 is even more preferable.

For conditional expression (4), it is more preferable to let the lower limit value to be 81, and 81.5 is even more preferable.

Moreover, for conditional expression (4), it is preferable to let the upper limit value to be 96, and to reduce a material cost by making so as not to exceed the upper limit value 96.

For conditional expression (5), it is more preferable to let the lower limit value to be 0.1, and 0.16 is even more preferable.

Moreover, for conditional expression (5), it is more preferable to let the upper limit value to be 0.6, and 0.4 is even more preferable.

For conditional expression (6), it is more preferable to let the lower limit value to be 0.4, and 0.5 is even more preferable.

Moreover, for conditional expression (6), it is more preferable to let the upper limit value to be 0.8, and 0.7 is even more preferable.

For conditional expression (7), it is more preferable to let the lower limit value to be 64°, and 70° is even more preferable.

Moreover, for conditional expression (8), it is more preferable to let the upper limit value to be 100°, and 90° is even more preferable.

For conditional expression (8), it is more preferable to let the lower limit value to be 1.0, and 1.2 is even more preferable.

Moreover, for conditional expression (8), it is more preferable to let the upper limit value to be 1.3.

Examples of the single focal length lenses will be described below in detail by referring to the accompanying diagrams. However, the present invention is not restricted to the examples described below.

It will be explained about the lens cross-sectional views of each of the examples. The lens cross-sectional views of each of the examples are a lens cross-sectional view at a time of focusing to an object at infinity. The aberration diagrams are an aberration diagram at a time of focusing to an object at infinity.

A first lens unit is denoted by G1, a second lens unit is denoted by G2, a third lens unit is denoted by G3, a fourth lens unit is denoted by G4, an aperture stop is denoted by S, and an image plane (an image pickup surface) is denoted by I. A cover glass is denoted by C, and is arranged between the fourth lens unit G4 and the image plane I.

It will be explained about the aberration diagrams of each of the examples.

FIG. 5A, FIG. 6A, FIG. 7A, and FIG. 8A show a spherical aberration (SA) at a time of focusing to an object at a short distance.

FIG. 5B, FIG. 6B, FIG. 7B, and FIG. 8B show an astigmatism (AS) at a time of focusing to an object at a short distance.

FIG. 5C, FIG. 6C, FIG. 7C, and FIG. 8C show a distortion (DT) at a time of focusing to an object at a short distance.

FIG. 5D, FIG. 6D, FIG. 7D, and FIG. 8D show a chromatic aberration of magnification (CC) at a time of focusing to an object at a short distance.

FIG. 5E, FIG. 6E, FIG. 7E, and FIG. 8E show a spherical aberration (SA) at a time of focusing to a near object.

FIG. 5F, FIG. 6F, FIG. 7F, and FIG. 8F show an astigmatism (AS) at a time of focusing to a near object.

FIG. 5G, FIG. 6G, FIG. 7G, and FIG. 8G show a distortion (DT) at a time of focusing to a near object.

FIG. 5H, FIG. 6H, FIG. 7H, and FIG. 8H show a chromatic aberration of magnification (CC) at a time of focusing to a near object.

FIG. 5I, FIG. 6I, FIG. 7I, and FIG. 8I show a spherical aberration (SA) at a time of focusing to an object at infinity.

FIG. 5J, FIG. 6J, FIG. 7J, and FIG. 8J show an astigmatism at a time of focusing to an object at infinity.

FIG. 5K, FIG. 6K, FIG. 7K, and FIG. 8K show a distortion (DT) at a time of focusing to an object at infinity.

FIG. 5L, FIG. 6L, FIG. 7L, and FIG. 8L show a chromatic aberration of magnification (CC) at a time of focusing to an object at infinity.

A single focal length lens according to an example 1 includes in order from an object side, a first lens unit G1 having a negative refractive power, a second lens unit G2 having a positive refractive power, a third lens unit G3 having negative refractive power, and a fourth lens unit G4 having a positive refractive power. An aperture stop S is disposed between the first lens unit G1 and the second lens unit G2.

The first lens unit G1 includes a negative meniscus lens L1 having a convex surface directed toward the object side, a negative meniscus lens L2 having a convex surface directed toward the object side, a biconcave negative lens L3, a biconvex positive lens L4, a biconvex positive lens L5, a biconcave negative lens L6, and a biconvex positive lens L7. Here, the biconcave negative lens L3 and the biconvex positive lens L4 are cemented. The biconvex positive lens L5, the biconcave negative lens L6, and the biconvex positive lens L7 are cemented.

The second lens unit G2 includes a biconvex positive lens L8, a biconvex positive lens L9, a positive meniscus lens L10 having a convex surface directed toward an image side, a negative meniscus lens L11 having a convex surface directed toward the image side, a positive meniscus lens L12 having convex surface directed toward the image side, and a biconvex positive lens L13. Here, the positive meniscus lens L10 and the negative meniscus lens L11 are cemented.

The third lens unit G3 includes a positive meniscus lens L14 having a convex surface directed toward the object side and a negative meniscus lens L15 having a convex surface directed toward the object side. Here, the positive meniscus lens L14 and the negative meniscus lens L15 are cemented.

The fourth lens unit G4 includes a biconvex positive lens L16.

The first lens unit G1 includes an object-side sub lens unit and an image-side sub lens unit. The object-side sub lens unit includes the negative meniscus lens L1 and the negative meniscus lens L2. The image-side sub lens unit includes the biconcave negative lens L3, the biconvex positive lens L4, the biconvex positive lens L5, the biconcave negative lens L6, and the biconvex positive lens L7.

The second lens unit G2 includes a first sub lens unit, a second sub lens unit, and a third sub lens unit. The first sub lens unit includes the biconvex positive lens L8 and the biconvex positive lens L9. The second sub lens unit includes the positive meniscus lens L10, the negative meniscus lens L11, and the positive meniscus lens L12. The third sub lens unit includes the biconvex positive lens L13.

At the time of focusing, the first lens unit G1, the second lens unit G2, and the fourth lens unit G4 do not move, but the third lens unit G3 moves. More specifically, at the time of focusing from an object at infinity to an object at a short distance, the third lens unit G3 moves toward the image side.

An aspheric surface is provided to a total of six surfaces namely, both surfaces of the negative meniscus lens L2, both surfaces of the biconvex positive lens L9, and both surfaces of the positive meniscus lens L12.

A single focal length lens according to an example 2 includes in order from an object side, a first lens unit G1 having a negative refractive power, a second lens unit G2 having a positive refractive power, a third lens unit G3 having a negative refractive power, and a fourth lens unit G4 having a positive refractive power. An aperture stop S is disposed between the first lens unit G1 and the second lens unit G2.

The first lens unit G1 includes a negative meniscus lens L1 having a convex surface directed toward the object side, a negative meniscus lens L2 having a convex surface directed toward the object side, a negative meniscus lens L3 having a convex surface directed toward an image side, a positive meniscus lens L4 having a convex surface directed toward the image side, a biconvex positive lens L5, a biconcave negative lens L6, and a biconvex positive lens L7. Here, the negative meniscus lens L3 and the positive meniscus lens L4 are cemented. The biconvex positive lens L5, the biconcave negative lens L6, and the biconvex positive lens L7 are cemented.

The second lens unit G2 includes a biconvex positive lens L8, a biconvex positive lens L9, a positive meniscus lens L10 having a convex surface directed toward the image side, a biconcave negative lens L11, a positive meniscus lens L12 having a convex surface directed toward the image side, and a biconvex positive lens L13. Here, the positive meniscus lens L10 and the biconcave negative lens L11 are cemented.

The third lens unit G3 includes a positive meniscus lens L14 having a convex surface directed toward the object side and a negative meniscus lens L15 having a convex surface directed toward the object side. Here, the positive meniscus lens L14 and the negative meniscus lens L15 are cemented.

The fourth lens unit G4 includes a biconvex positive lens L16.

The first lens unit G1 includes an object-side sub lens unit and an image-side sub lens unit. The object-side sub lens unit includes the negative meniscus lens L1 and the negative meniscus lens L2. The image-side sub lens unit includes the negative meniscus lens L3, the positive meniscus lens L4, the biconvex positive lens L5, the biconcave negative lens L6, and the biconvex positive lens L7.

The second lens unit G2 includes a first sub lens unit, a second sub lens unit, and a third sub lens unit. The first sub lens unit includes the biconvex positive lens L8 and the biconvex positive lens L9. The second sub lens unit includes the positive meniscus lens L10, the biconcave negative lens L11, and the positive meniscus lens L12. The third sub lens unit includes the biconvex positive lens L13.

At the time of focusing, the first lens unit G1, the second lens unit G2, and the fourth lens unit G4 do not move, but the third lens unit G3 moves. More specifically, at the time of focusing from an object at infinity to an object at a short distance, the third lens unit G3 moves toward the image side.

An aspheric surface is provided to a total of six surfaces namely, both surfaces of the negative meniscus lens L2, both surfaces of the positive meniscus lens L12, and both surfaces of the biconvex positive lens L13.

A single focal length lens according to an example 3 includes in order from an object side, a first lens unit G1 having a negative refractive power, a second lens unit G2 having a positive refractive power, a third lens unit G3 having a negative refractive power, and a fourth lens unit G4 having a positive refractive power. An aperture stop S is disposed between the first lens unit G1 and the second lens unit G2.

The first lens unit G1 includes a negative meniscus lens L1 having a convex surface directed toward the object side, a negative meniscus lens L2 having a convex surface directed toward the object side, a biconvex positive lens L3, a biconcave negative lens L4, a biconcave negative lens L5, a biconvex positive lens L6, and a positive meniscus lens L7 having a convex surface directed toward an image side. Here, the biconvex positive lens L3 and the biconcave negative lens L4 are cemented. The biconcave negative lens L5 and the biconvex positive lens L6 are cemented.

The second lens unit G2 includes a biconvex positive lens L8, a biconvex positive lens L9, a negative meniscus lens L10 having a convex surface directed toward the image side, a negative meniscus lens L11 having a convex surface directed toward the object side, and a biconvex positive lens L12. Here, the biconvex positive lens L9 and the negative meniscus lens L10 are cemented.

The third lens unit G3 includes a biconvex positive lens L13 and a biconcave negative lens L14. Here, the biconvex positive lens L13 and the biconcave negative lens L14 are cemented.

The fourth lens unit G4 includes a biconvex positive lens L15.

The first lens unit G1 includes an object-side sub lens unit and an image-side sub lens unit. The object-side sub lens unit includes the negative meniscus lens L1, the negative meniscus lens L2, the biconvex positive lens L3, and the biconcave negative lens L4. The image-side sub lens unit includes the biconcave negative lens L5, the biconvex positive lens L6, and the positive meniscus lens L7.

The second lens unit G2 includes a first sub lens unit, a second sub lens unit, and a third sub lens unit. The first sub lens unit includes the biconvex positive lens L8, the biconvex positive lens L9, and the negative meniscus lens L10. The second sub lens unit includes the negative meniscus lens L11. The third sub lens unit includes the biconvex positive lens L12.

At the time of focusing, the first lens unit G1, the second lens unit G2, and the fourth lens unit G4 do not move, but the third lens unit G3 moves. More specifically, at the time of focusing from an object at infinity to an object at a short distance, the third lens unit G3 moves toward the image side.

An aspheric surface is provided to a total of six surfaces namely, both surfaces of the negative meniscus lens L2, both surfaces of the negative meniscus lens L11, and both surfaces of the biconvex positive lens L12.

A single focal length lens according to an example 4 includes in order from an object side, a first lens unit G1 having a negative refractive power, a second lens unit G2 having a positive refractive power, a third lens unit G3 having a negative refractive power, and a fourth lens unit G4 having a positive refractive power. An aperture stop S is disposed between the first lens unit G1 and the second lens unit G2.

The first lens unit G1 includes a negative meniscus lens L1 having a convex surface directed toward the object side, a negative meniscus lens L2 having a convex surface directed toward the object side, a biconvex positive lens L3, a biconcave negative lens L4, a biconcave negative lens L5, a biconvex positive lens L6, and a positive meniscus lens L7 having a convex surface directed toward an image side. Here, the biconvex positive lens L3 and the biconcave negative lens L4 are cemented. The biconcave negative lens L5 and the biconvex positive lens L6 are cemented.

The second lens unit G2 includes a biconvex positive lens L8, a negative meniscus lens L9 having a convex surface directed toward the object side, a biconvex positive lens L10, a negative meniscus lens L11 having a convex surface directed toward the object side, and a biconvex positive lens L12. Here, the negative meniscus lens L9 and the biconvex positive lens L10 are cemented.

The third lens unit G3 includes a biconvex positive lens L13 and a biconcave negative lens L14. Here, the biconvex positive lens L13 and the biconcave negative lens L14 are cemented.

The fourth lens unit G4 includes a biconvex positive lens L15.

The first lens unit G1 includes an object-side sub lens unit and an image-side sub lens unit. The object-side sub lens unit includes the negative meniscus lens L1, the negative meniscus lens L2, the biconvex positive lens L3, and the biconcave negative lens L4. The image-side sub lens unit includes the biconcave negative lens L5, the biconvex positive lens L6, and the positive meniscus lens L7.

The second lens unit G2 includes a first sub lens unit, a second sub lens unit, and a third sub lens unit. The first sub lens unit includes the biconvex positive lens L8, the negative meniscus lens L9, and the biconvex positive lens L10. The second sub lens unit includes the negative meniscus lens L11. The third sub lens unit includes the biconvex positive lens L12.

At the time of focusing, the first lens unit G1, the second lens unit G2, and the fourth lens unit G4 do not move, but the third lens unit G3 moves. More specifically, at the time of focusing from an object at infinity to an object at a short distance, the third lens unit G3 moves toward the image side.

An aspheric surface is provided to a total of six surfaces namely, both surfaces of the negative meniscus lens L2, both surfaces of the negative meniscus lens L11, and both surfaces of the biconvex positive lens L12.

Numerical data of each example described above is shown below. In Surface data, r denotes radius of curvature of each lens surface, d denotes a distance between respective lens surfaces, nd denotes a refractive index of each lens for a d-line, vd denotes an Abbe number for each lens and * denotes an aspheric surface.

Further, in Various data, INF denotes that an object positioned at infinity, CL1 denotes that the object positioned at short distance, and CL2 denotes that the object positioned at close distance. Moreover, β denotes a magnification of photographing, f denotes a focal length of the entire system, FNO. denotes an F-number, ω denotes a half angle of view, IH denotes an image height, φ denotes a diameter of a aperture stop, and d0 denotes a distance to an object plane.

Further, in Unit focal length, each of f1, f2 . . . is a focal length of each lens unit.

A shape of an aspherical surface is defined by the following expression where the direction of the optical axis is represented by z, the direction orthogonal to the optical axis is represented by y, a conical coefficient is represented by K, aspheric surface coefficients are represented by A4, A6, A8, A10, A12 . . .

$$Z=(y^2/r)/[1+\{1-(1+k)(y/r)^2\}^{1/2}]+A4y^4+A6y^6+A8y^8+A10y^{10}+A12y^{12}+\ldots$$

Further, in the aspherical surface coefficients, 'E-n' (where, n is an integral number) indicates '$10^{-n}$'. Moreover, these symbols are commonly used in the following numerical data for each example.

Example 1

| Unit mm | | | | |
|---|---|---|---|---|
| Surface data | | | | |
| Surface no. | r | d | nd | vd |
| Object plane | ∞ | Variable | | |
| 1 | 36.299 | 2.50 | 1.48749 | 70.23 |
| 2 | 15.371 | 6.04 | | |
| 3* | 34.878 | 3.00 | 1.49700 | 81.61 |
| 4* | 11.582 | 15.06 | | |
| 5 | −22.117 | 1.50 | 1.80400 | 46.57 |
| 6 | 312.545 | 2.50 | 1.84666 | 23.78 |
| 7 | −62.694 | 0.20 | | |
| 8 | 89.489 | 6.50 | 1.65844 | 50.86 |
| 9 | −20.410 | 1.50 | 1.69895 | 30.13 |
| 10 | 178.097 | 3.90 | 1.43875 | 94.93 |

-continued

| Unit mm | | | | |
|---|---|---|---|---|
| 11 | −48.985 | 1.00 | | |
| 12 (Stop) | ∞ | 1.25 | | |
| 13 | 71.395 | 4.31 | 1.80518 | 25.42 |
| 14 | −99.001 | 0.20 | | |
| 15* | 57.394 | 6.60 | 1.49700 | 81.61 |
| 16* | −56.686 | 2.74 | | |
| 17 | −195.611 | 5.83 | 1.43875 | 94.93 |
| 18 | −23.388 | 1.50 | 1.66680 | 33.05 |
| 19 | −651.528 | 1.96 | | |
| 20* | −67.770 | 2.00 | 1.80610 | 40.88 |
| 21* | −43.920 | 0.20 | | |
| 22 | 44.727 | 7.79 | 1.49700 | 81.61 |
| 23 | −24.863 | Variable | | |
| 24 | 71.748 | 1.87 | 1.49700 | 81.61 |
| 25 | 100.000 | 0.80 | 1.71736 | 29.52 |
| 26 | 18.234 | Variable | | |
| 27 | 43.450 | 3.88 | 1.49700 | 81.61 |
| 28 | −49.551 | 9.40 | | |
| 29 | ∞ | 4.11 | 1.51633 | 64.14 |
| 30 | ∞ | 2.05 | | |
| Image pickup surface | ∞ | | | |

| Aspherical surface data |
|---|
| 3rd surface |
| k = 0.000<br>A4 = −8.54431e−07, A6 = 2.92406e−08, A8 = 8.71166e−12,<br>A10 = 5.96446e−14 |
| 4th surface |
| k = −0.915<br>A4 = 2.98400e−05, A6 = 5.87514e−08, A8 = 5.70905e−10,<br>A10 = −3.59278e−13 |
| 15th surface |
| k = 0.000<br>A4 = 1.16127e−06, A6 = −3.18739e−09, A8 = 2.26403e−12 |
| 16th surface |
| k = 0.000<br>A4 = 6.73233e−06, A6 = −3.06451e−08, A8 = 5.06806e−11 |
| 20th surface |
| k = 0.000<br>A4 = −8.16392e−06, A6 = −5.09021e−08, A8 = 1.56178e−10 |
| 21th surface |
| k = 0.000<br>A4 = 1.79292e−05, A6 = −1.71235e−08, A8 = 1.86557e−10 |

| Various data | | | |
|---|---|---|---|
| | INF | CL1 | CL2 |
| β | 0 | −0.02 | −0.11 |
| f | 12.24 | 12.19 | 11.95 |
| FNO. | 1.24 | 1.24 | 1.23 |
| 2ω | 82.90 | 83.03 | 83.69 |
| IH | 10.14 | 10.14 | 10.14 |
| φ | 29.30 | 29.30 | 29.30 |
| d0 | ∞ | 591.98 | 91.99 |
| d23 | 2.00 | 2.22 | 3.19 |
| d26 | 5.83 | 5.61 | 4.64 |

-continued

Unit mm

Unit focal length f1 = −17.89 f2 = 23.29 f3 = −33.64 f4 = 47.23 f12 = 9.68

Example 2

Unit mm

Surface data

| Surface no. | r | d | nd | νd |
|---|---|---|---|---|
| Object plane | ∞ | Variable | | |
| 1 | 33.043 | 2.75 | 1.59282 | 68.63 |
| 2 | 15.055 | 5.47 | | |
| 3* | 32.816 | 3.00 | 1.49700 | 81.61 |
| 4* | 11.820 | 12.92 | | |
| 5 | −18.331 | 1.51 | 1.80400 | 46.57 |
| 6 | −103.368 | 2.85 | 1.84666 | 23.78 |
| 7 | −31.726 | 0.23 | | |
| 8 | 82.178 | 7.23 | 1.64850 | 53.02 |
| 9 | −17.280 | 1.50 | 1.69895 | 30.13 |
| 10 | 73.656 | 2.79 | 1.43875 | 94.93 |
| 11 | −610.867 | 1.00 | | |
| 12 (Stop) | ∞ | 1.50 | | |
| 13 | 56.879 | 5.30 | 1.80518 | 25.42 |
| 14 | −59.444 | 0.20 | | |
| 15 | 46.254 | 5.58 | 1.49700 | 81.61 |
| 16 | −65.174 | 2.14 | | |
| 17 | −160.136 | 6.00 | 1.43875 | 94.93 |
| 18 | −20.354 | 1.50 | 1.66680 | 33.05 |
| 19 | 42.211 | 2.43 | | |
| 20* | −2987.084 | 3.24 | 1.80610 | 40.88 |
| 21* | −70.729 | 0.20 | | |
| 22* | 29.292 | 8.51 | 1.49700 | 81.61 |
| 23* | −25.097 | Variable | | |
| 24 | 62.146 | 2.00 | 1.59282 | 68.63 |
| 25 | 105.744 | 0.80 | 1.66680 | 33.05 |
| 26 | 19.165 | Variable | | |
| 27 | 37.666 | 4.00 | 1.49700 | 81.61 |
| 28 | −55.696 | 9.40 | | |
| 29 | ∞ | 4.11 | 1.51633 | 64.14 |
| 30 | ∞ | 2.05 | | |
| Image pickup surface | ∞ | | | |

Aspherical surface data

3rd surface k = 0.000
A4 = 4.25777e−06, A6 = 2.71488e−08, A8 = 2.37707e−10,
A10 = −1.31085e−13
4th surface k = −1.060
A4 = 3.84307e−05, A6 = 1.52123e−08, A8 = 1.39055e−09,
A10 = −8.18815e−13
20th surface k = 0.000
A4 = −1.91140e−05, A6 = 6.65182e−08, A8 = 1.81417e−10,
A10 = −2.82387e−13
21th surface k = 0.000
A4 = 5.42178e−06, A6 = 5.18614e−08, A8 = 3.35488e−10,
A10 = −8.59916e−13
22th surface k = 0.000
A4 = 2.11946e−06, A6 = −2.98337e−08, A8 = 3.43568e−11

-continued

Unit mm

23th surface k = 0.000
A4 = 1.05949e−05, A6 = −2.62754e−08, A8 = 9.64274e−11

Various data

| | INF | CL1 | CL2 |
|---|---|---|---|
| β | 0 | −0.02 | −0.11 |
| f | 12.24 | 12.20 | 11.97 |
| FNO. | 1.26 | 1.26 | 1.24 |
| 2ω | 85.23 | 85.40 | 86.16 |
| IH | 10.47 | 10.45 | 10.48 |
| φ | 26.94 | 26.94 | 26.94 |
| d0 | ∞ | 592.63 | 91.99 |
| d23 | 1.98 | 2.27 | 3.62 |
| d26 | 5.80 | 5.51 | 4.17 |

Unit focal length f1 = −14.47 f2 = 23.86 f3 = −41.71 f4 = 45.86 f2 = 10.82

Example 3

Unit mm

Surface data

| Surface no. | r | d | nd | νd |
|---|---|---|---|---|
| Object plane | ∞ | Variable | | |
| 1 | 32.026 | 2.50 | 1.48749 | 70.23 |
| 2 | 15.890 | 6.59 | | |
| 3* | 49.380 | 2.50 | 1.49700 | 81.61 |
| 4* | 14.883 | 3.78 | | |
| 5 | 36.123 | 5.50 | 2.00100 | 29.13 |
| 6 | −46.913 | 1.27 | 1.63980 | 34.46 |
| 7 | 22.472 | 6.10 | | |
| 8 | −17.446 | 1.50 | 1.67300 | 38.15 |
| 9 | 99.740 | 3.00 | 1.59349 | 67.00 |
| 10 | −152.014 | 0.23 | | |
| 11 | −672.762 | 4.69 | 1.76200 | 40.10 |
| 12 | −28.555 | 1.00 | | |
| 13 (Stop) | ∞ | 1.50 | | |
| 14 | 44.126 | 8.18 | 1.59282 | 68.63 |
| 15 | −44.126 | 0.20 | | |
| 16 | 81.931 | 6.16 | 1.43700 | 95.10 |
| 17 | −45.479 | 1.47 | 1.80518 | 25.42 |
| 18 | −140.099 | 0.20 | | |
| 19* | 46.606 | 2.50 | 1.74320 | 49.34 |
| 20* | 32.114 | 2.48 | | |
| 21* | 47.549 | 8.52 | 1.49700 | 81.61 |
| 22* | −28.010 | Variable | | |
| 23 | 167.629 | 2.05 | 1.84666 | 23.78 |
| 24 | −167.629 | 1.00 | 1.67270 | 32.10 |
| 25 | 20.452 | Variable | | |
| 26 | 30.472 | 4.88 | 1.59282 | 68.63 |
| 27 | −58.696 | 11.14 | | |
| 28 | ∞ | 4.11 | 1.51633 | 64.14 |
| 29 | ∞ | 2.05 | | |
| Image pickup surface | ∞ | | | |

Aspherical surface data

3rd surface k = 0.000
A4 = 1.10200e−05, A6 = −2.61980e−08, A8 = 1.23579e−10

-continued

Unit mm

4th surface k = −1.010
A4 = 3.30747e−05, A6 = −9.37804e−09, A8 = 8.11522e−11
19th surface k = 0.000
A4 = 1.16974e−05, A6 = −7.20617e−08, A8 = −6.22130e−11
20th surface k = 0.000
A4 = 3.12669e−05, A6 = −3.36762e−08, A8 = 1.97108e−11
21th surface k = 0.000
A4 = 5.76048e−06, A6 = 3.94500e−08, A8 = 1.11640e−10
22th surface k = 0.000
A4 = 1.09484e−05, A6 = −2.61853e−08, A8 = 7.66353e−12

Various data

|   | INF | CL1 | CL2 |
|---|---|---|---|
| β | 0 | −0.02 | −0.15 |
| f | 17.15 | 17.12 | 16.82 |
| FNO. | 1.26 | 1.26 | 1.25 |
| 2ω | 66.07 | 66.10 | 66.10 |
| IH | 10.87 | 10.95 | 10.86 |
| φ | 28.82 | 28.82 | 28.82 |
| d0 | ∞ | 837.06 | 94.99 |
| d22 | 1.98 | 2.36 | 4.92 |
| d25 | 7.91 | 7.53 | 4.97 |

Unit focal length f1 = −30.97 f2 = 25.12 f3 = −37.73 f4 = 34.54 f12 = 16.09

Example 4

Unit mm

Surface data

| Surface no. | r | d | nd | vd |
|---|---|---|---|---|
| Object plane | ∞ | Variable | | |
| 1 | 34.060 | 2.48 | 1.48749 | 70.23 |
| 2 | 15.890 | 6.27 | | |
| 3* | 36.526 | 2.50 | 1.49700 | 81.61 |
| 4* | 14.421 | 4.13 | | |
| 5 | 40.489 | 5.59 | 2.00100 | 29.13 |
| 6 | −40.489 | 1.30 | 1.60342 | 38.03 |
| 7 | 21.327 | 5.94 | | |
| 8 | −18.152 | 1.50 | 1.67300 | 38.15 |
| 9 | 51.277 | 4.81 | 1.59282 | 68.63 |
| 10 | −51.277 | 0.24 | | |
| 11 | −86.319 | 4.02 | 1.76200 | 40.10 |
| 12 | −27.680 | 1.00 | | |
| 13 (Stop) | ∞ | 1.50 | | |
| 14 | 48.618 | 7.37 | 1.59282 | 68.63 |
| 15 | −48.618 | 0.20 | | |
| 16 | 76.695 | 1.59 | 1.84666 | 23.78 |
| 17 | 45.653 | 5.54 | 1.43700 | 95.10 |
| 18 | −94.330 | 0.20 | | |
| 19* | 81.029 | 2.49 | 1.74320 | 49.34 |
| 20* | 38.257 | 2.66 | | |
| 21* | 51.308 | 8.63 | 1.49700 | 81.61 |
| 22* | −26.655 | Variable | | |
| 23 | 247.923 | 2.14 | 1.85025 | 30.05 |
| 24 | −99.447 | 1.00 | 1.66680 | 33.05 |
| 25 | 19.800 | Variable | | |

-continued

Unit mm

| 26 | 29.883 | 5.18 | 1.59282 | 68.63 |
|---|---|---|---|---|
| 27 | −53.477 | 11.00 | | |
| 28 | ∞ | 4.11 | 1.51633 | 64.14 |
| 29 | ∞ | 2.05 | | |
| Image pickup surface | ∞ | | | |

Aspherical surface data

3rd surface k = 0.000
A4 = 6.39453e−06, A6 = −5.82819e−08, A8 = 1.46593e−10
4th surface k = −0.828
A4 = 2.81137e−05, A6 = −6.66953e−08, A8 = 2.46322e−13
19th surface k = 0.000
A4 = −3.96187e−07, A6 = 1.84354e−08, A8 = −1.16042e−10
20th surface k = 0.000
A4 = 1.87054e−05, A6 = 8.61743e−08, A8 = −4.73479e−11
21th surface k = 0.000
A4 = 1.05728e−05, A6 = 7.42740e−08, A8 = −4.38814e−11
22th surface k = 0.000
A4 = 1.35526e−05, A6 = −2.20924e−08, A8 = −2.06785e−11

Various data

|   | INF | CL1 | CL2 |
|---|---|---|---|
| β | 0 | −0.02 | −0.15 |
| f | 16.67 | 16.65 | 16.39 |
| FNO. | 1.24 | 1.24 | 1.25 |
| 2ω | 67.55 | 67.60 | 67.51 |
| IH | 10.81 | 10.89 | 10.79 |
| φ | 28.98 | 28.98 | 28.98 |
| d0 | ∞ | 813.34 | 94.99 |
| d22 | 1.98 | 2.34 | 4.65 |
| d25 | 7.57 | 7.21 | 4.91 |

Unit focal length f1 = −36.72 f2 = 25.72 f3 = −35.50 f4 = 33.10 f12 = 15.53

Next, values of conditional expressions in each example are given below.

| Conditional expression | Example 1 | Example 2 | Example 3 | Example 4 |
|---|---|---|---|---|
| (1) f1/f | −1.461 | −1.182 | −1.806 | −2.203 |
| (2) f3/f | −2.748 | −3.407 | −2.200 | −2.129 |
| (3) f12/f | 0.790 | 0.884 | 0.938 | 0.931 |
| (4) vd2p | 81.61 | 81.61 | 94.93 | 94.93 |
|  | 94.93 | 94.93 | 81.61 | 81.61 |
|  | 81.61 | 81.61 | | |
| (5) Dm/St | 0.199 | 0.215 | 0.274 | 0.261 |
| (6) DA/DL | 0.652 | 0.579 | 0.574 | 0.565 |
| (7) 2ω | 82.90 | 85.23 | 66.07 | 67.55 |
| (8) FNOm | 1.240 | 1.260 | 1.260 | 1.240 |

Values of parameters are given below.

|      | Example 1 | Example 2 | Example 3 | Example 4 |
|------|-----------|-----------|-----------|-----------|
| f    | 12.241    | 12.242    | 17.148    | 16.671    |
| FNOm | 1.240     | 1.260     | 1.260     | 1.240     |
| f1   | −17.885   | −14.473   | −30.968   | −36.722   |
| f2   | 23.293    | 23.862    | 25.118    | 25.717    |
| f3   | −33.643   | −41.710   | −37.729   | −35.499   |
| f4   | 47.234    | 45.864    | 34.540    | 33.103    |
| f12  | 9.676     | 10.818    | 16.089    | 15.529    |
| Dm   | 5.828     | 5.803     | 7.908     | 7.569     |
| St   | 29.298    | 26.944    | 28.824    | 28.980    |
| DA   | 36.4688   | 33.8925   | 31.9695   | 31.6987   |
| DL   | 55.9712   | 58.5476   | 55.7351   | 56.1414   |

The optical apparatus of the present embodiment includes an image pickup apparatus and a protection apparatus. Concrete examples of the image pickup apparatus and the projection apparatus will be described below.

Figure 9:
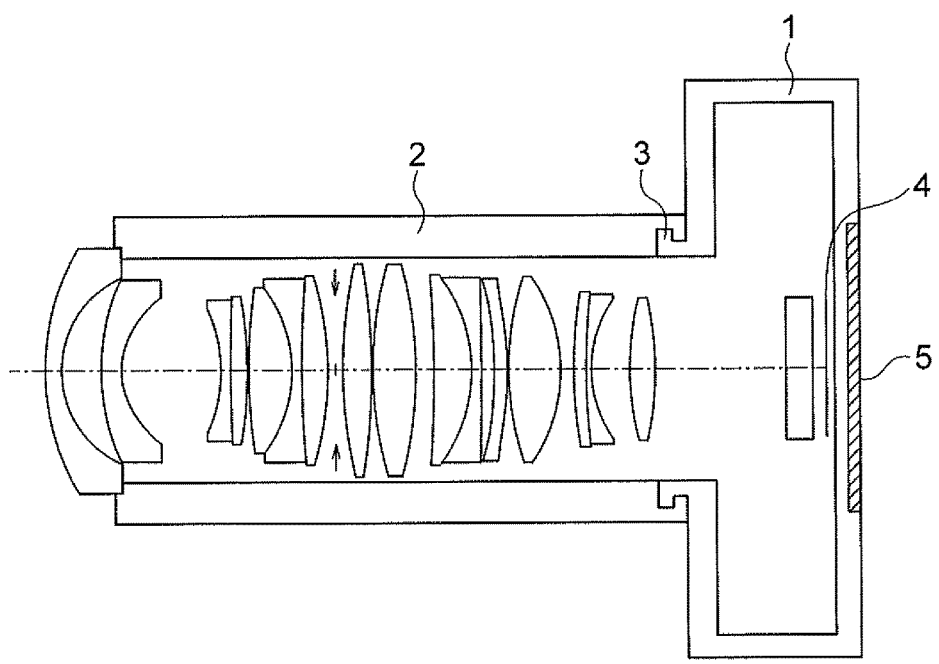
FIG. 9 is a cross-sectional view of an image pickup apparatus.

FIG. 9 is a cross-sectional view of a single-lens mirrorless camera as an electronic image pickup apparatus. In FIG. 9, a photographic optical system 2 is disposed inside a lens barrel of a single-lens mirrorless camera 1. A mount portion 3 enables the photographic optical system 2 to be detachable from a body of the single-lens mirrorless camera 1. As the mount portion 3, a mount such as a screw-type mount and a bayonet-type mount is to be used. In this example, a bayonet-type mount is used. Moreover, an image pickup element surface 4 and a back monitor 5 are disposed in the body of the single-lens mirrorless camera 1. As an image pickup element, an element such as a small-size CCD (charge coupled device) or a CMOS (complementary metal-oxide semiconductor) is to be used.

Moreover, as the photographic optical system 2 of the single-lens mirrorless camera 1, the single focal length lens described in any one of the examples from the first example to the fourth example is to be used.

Figure 10:
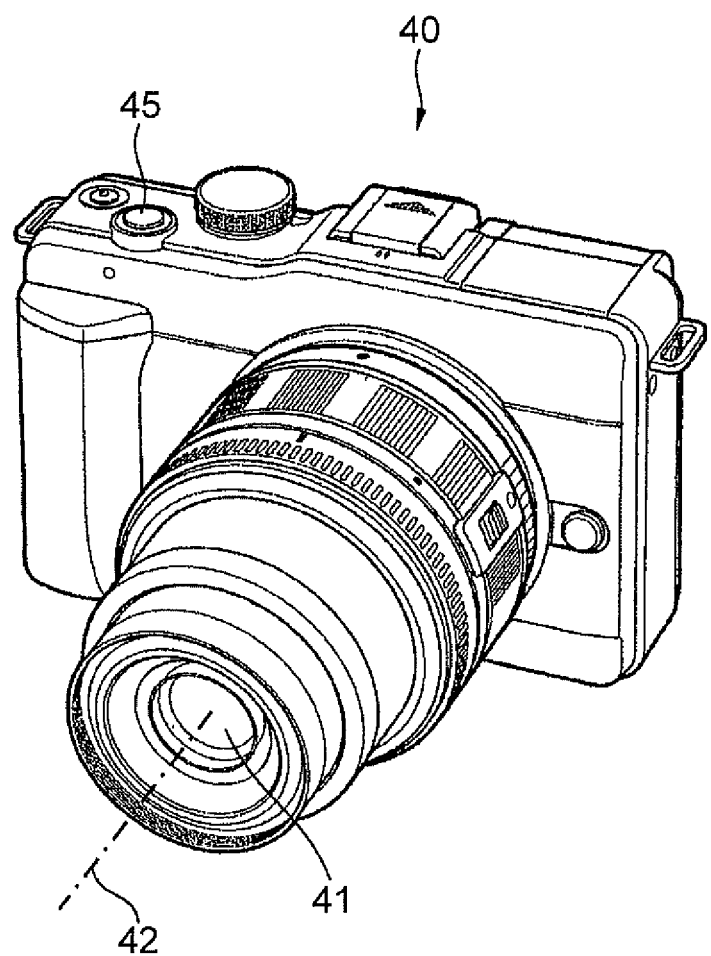
FIG. 10 is a front perspective view of the image pickup apparatus.
Figure 11:
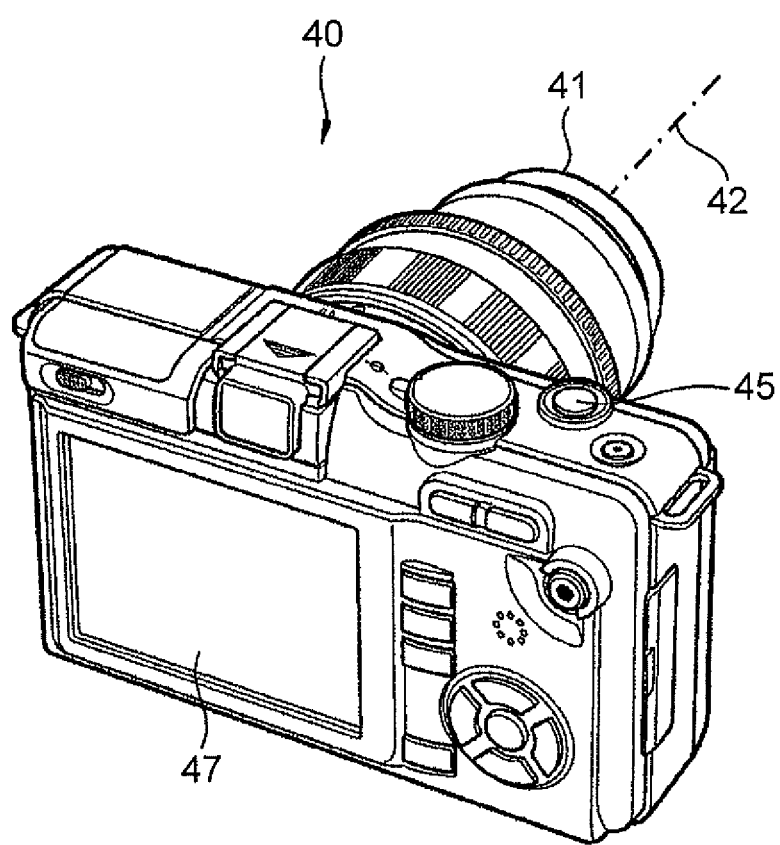
FIG. 11 is a rear perspective view of the image pickup apparatus.

FIG. 10 and FIG. 11 are conceptual diagrams of an arrangement of the image pickup apparatus. FIG. 10 is a front perspective view of a single-lens mirrorless camera 40 as the image pickup apparatus, and FIG. 11 is a rear perspective view of the single-lens mirrorless camera 40. The single focal length lens described in any one of is used in a photographic optical system 41 of the single-lens mirrorless camera 40.

The single-lens mirrorless camera 40 according to the present embodiment includes the photographic optical system 41 which is positioned in a photographic optical path 42, a shutter button 45, and a liquid-crystal display monitor 47. As the shutter button 45 disposed on an upper portion of the single-lens mirrorless camera 40 is pressed, in conjunction with the pressing of the shutter button 45, photography is carried out by the photographic optical system 41 such as the single focal length lens according to the first example. An object image which is formed by the photographic optical system 41 is formed on an image pickup element (photo-electric conversion surface) which is provided near an image forming surface. The object image which has been received optically by the image pickup element is displayed on the liquid-crystal display monitor 47 which is provided to a rear surface of the camera, as an electronic image by a processing means. Moreover, it is possible to record the electronic image which has been photographed, in a storage means.

Figure 12:
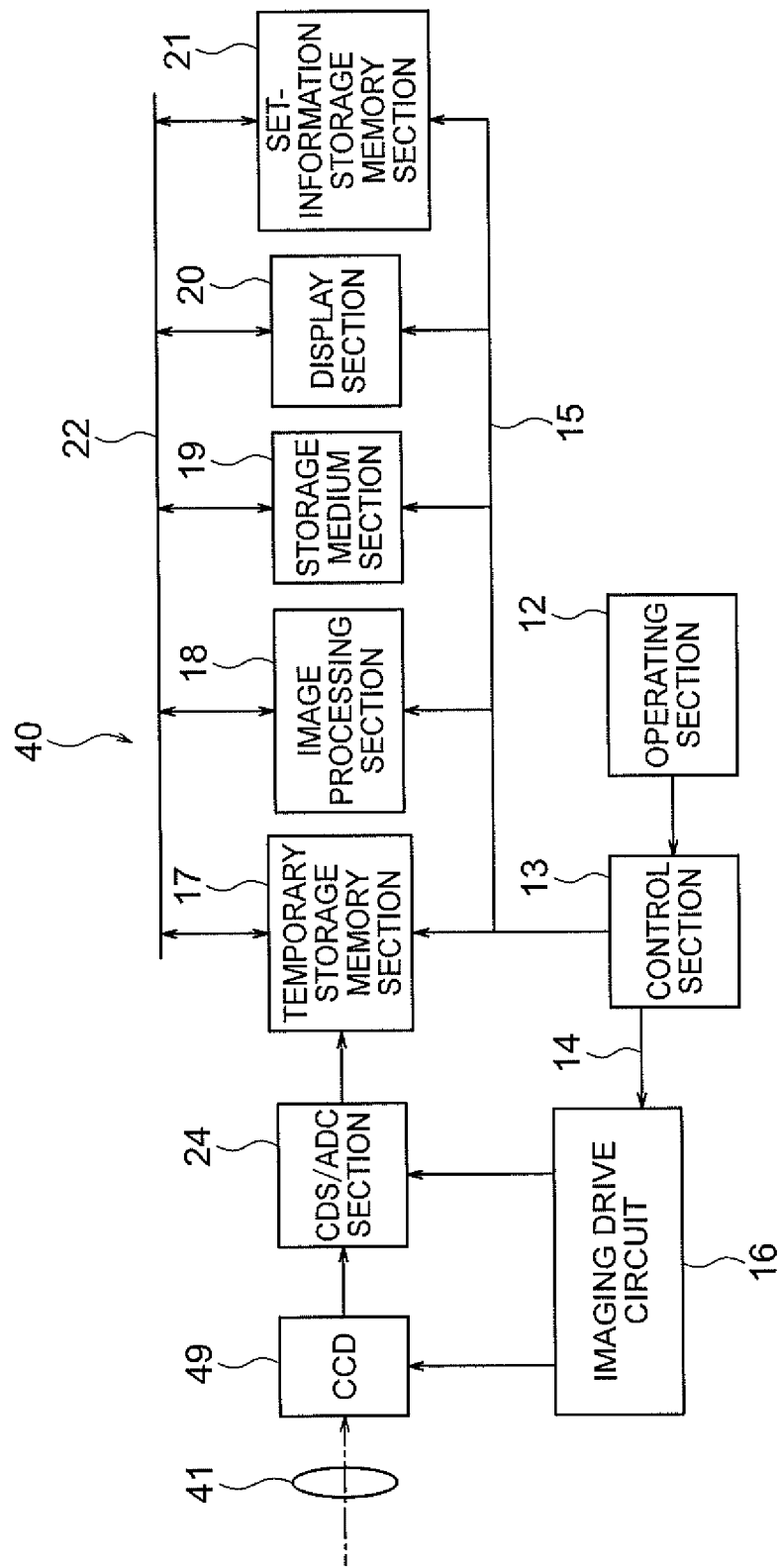
FIG. 12 is a schematic block diagram of an internal circuit of main components of the image pickup apparatus.

FIG. 12 is a structural block diagram of an internal circuit of main components of the single-lens mirrorless camera 40. In the following description, the processing means described above includes for instance, a CDS/ADC section 24, a temporary storage memory 17, and an image processing section 18, and a storage means consists of a storage medium section 19 for example.

As shown in FIG. 12, the single-lens mirrorless camera 40 includes an operating section 12, a control section 13 which is connected to the operating section 12, the temporary storage memory 17 and an imaging drive circuit 16 which are connected to a control-signal output port of the control section 13, via a bus 14 and a bus 15, the image processing section 18, the storage medium section 19, a display section 20, and a set-information storage memory section 21.

The temporary storage memory 17, the image processing section 18, the storage medium section 19, the display section 20, and the set-information storage memory section 21 are structured to be capable of mutually inputting and outputting data via a bus 22. Moreover, the CCD 49 and the CDS/ADC section 24 are connected to the imaging drive circuit 16.

The operating section 12 includes various input buttons and switches, and informs the control section 13 of event information which is input from outside (by a user of the camera) via these input buttons and switches. The control section 13 is a central processing unit (CPU), and has a built-in computer program memory which is not shown in the diagram. The control section 13 controls the entire single-lens mirrorless camera 40 according to a computer program stored in this computer program memory.

The CCD 49 is driven and controlled by the imaging drive circuit 16, and which converts an amount of light for each pixel of the object image formed by the photographic optical system 41 to an electric signal, and outputs to the CDS/ADC section 24.

The CDS/ADC section 24 is a circuit which amplifies the electric signal which is input from the CCD 49, and carries out analog/digital conversion, and outputs to the temporary storage memory 17 image raw data (Bayer data, hereinafter called as 'RAW data') which is only amplified and converted to digital data.

The temporary storage memory 17 is a buffer which includes an SCRAM (Synchronous Dynamic Random Access Memory) for example, and is a memory device which stores temporarily the RAW data which is output from the CDS/ADC section 24. The image processing section 18 is a circuit which reads the RAW data stored in the temporary storage memory 17, or the RAW data stored in the storage medium section 19, and carries out electrically various image-processing including the distortion correction, based on image-quality parameters specified by the control section 13.

The storage medium section 19 is a recording medium in the form of a card or a stick including a flash memory for instance, detachably mounted. The storage medium section 19 records and maintains the RAW data transferred from the temporary storage memory 17 and image data subjected to image processing in the image processing section 18 in the card flash memory and the stick flash memory.

The display 20 includes the liquid-crystal display monitor, and displays photographed RAW data, image data and operation menu on the liquid-crystal display monitor. The set-information storage memory section 21 includes a ROM section in which various image quality parameters are stored in advance, and a RAM section which stores image quality parameters which are selected by an input operation on the operating section 12, from among the image quality parameters which are read from the ROM section.

In the single-lens mirrorless camera 40 in which such an arrangement is made, by adopting the single focal length lens according to the present invention as the photographing optical system 41, it is possible to capture an image in a wide photography range with low noise at high resolution. Moreover, it is possible to use the single focal length lens according to the present invention in an image pickup apparatus of a type having a quick-return mirror.

Figure 13:
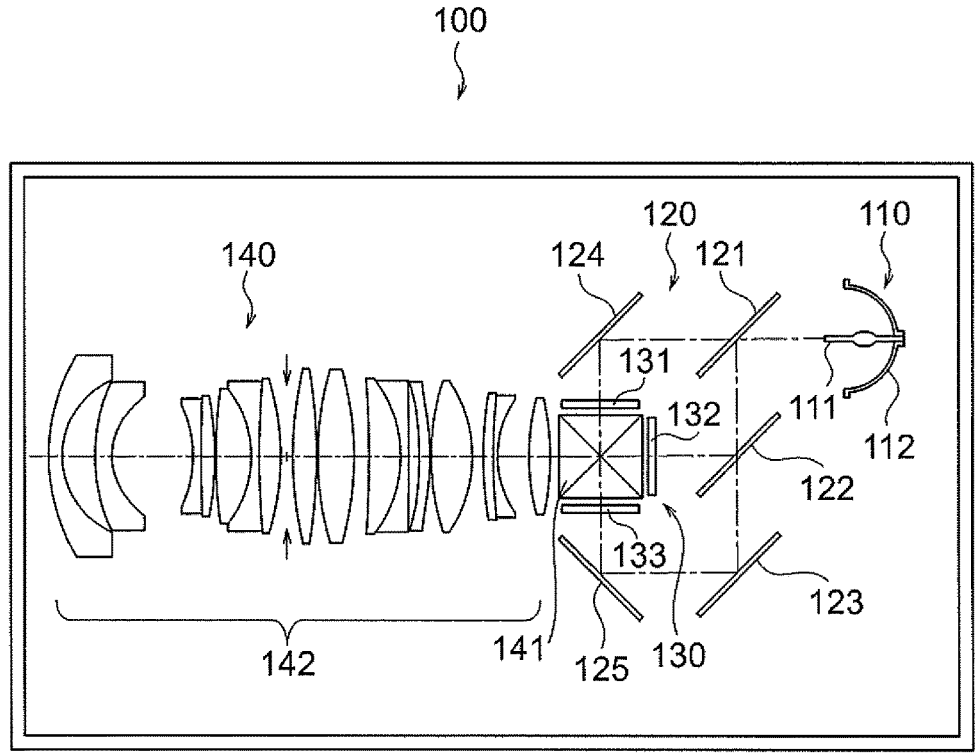
FIG. 13 is a cross-sectional view of a projection apparatus.

FIG. 13 is a sectional view of a projector as a projection apparatus. As illustrated in FIG. 13, a projector 100 includes a light source unit 110, an illumination unit 120, an image forming unit 130, and a projection unit 140.

The light source unit 110 includes a light source 111 and a reflective member 112. Illumination light is emitted from the light source 111. The illumination light is white light. The illumination light is reflected by the reflective member 112 and enters the illumination unit 120.

The illumination unit 120 includes a first dichroic mirror 121, a second dichroic mirror 122, a third dichroic mirror 123, a first reflective member 124, and a second reflective member 125.

In the first dichroic mirror 121, light in the red wavelength range (hereinafter referred to as "red light") is transmitted, and light in the other wavelength ranges is reflected. In the second dichroic mirror 122, light in the green wavelength range (hereinafter referred to as "green light") is reflected, and light in the other wavelength ranges is transmitted. In the third dichroic mirror 123, light in the blue wavelength range (hereinafter referred to as "blue light") is reflected, and light in the other wavelength ranges is transmitted. The red light, the green light, and the blue light enter the image forming unit 130. A general plane reflector may be used instead of the third dichroic mirror 123.

The image forming unit 130 has a first display element 131, a second display element 132, and a third display element 133.

The first display element 131 is irradiated with red light through the first reflective member 124. The second display element 132 is irradiated with green light. The third display element 133 is irradiated with blue light through the second reflective member 125.

Here, an identical image is displayed on the first display element 131, the second display element 132, and the third display element 133. Thus, a red image is displayed on the first display element 131, a green image is displayed on the second display element 132, and a blue image is displayed on the third display element 133.

Lights emitted from the first display element 131, the second display element 132, and the third display element 133 enter the projection unit 140.

The projection unit 140 includes a dichroic prism 141 and a projection optical system 142.

Lights emitted from the first display element 131, the second display element 132, and the third display element 133 are combined in the dichroic prism 141. As described above, a red image, a green image, and a blue image are displayed in the image forming unit 130. The three images are combined by the dichroic prism 141.

The projection optical system 142 projects the combined three images to a predetermined position. For example, the single focal length lens illustrated in any one of examples from first examples to fourth example above is used for this projection optical system 142.

The image forming unit 130 may be a light valve such as a digital micromirror device (DMD). In this case, light from the light source unit 110 is reflected by the light valve, and the image from the light valve is magnified and projected by the projection unit 140.

In the projector 100 thus configured, the single focal length lens of the present invention is employed as the projection optical system 142, whereby it is possible to project an image in a wide projection range with low noise at high resolution.

An optical system to be used in an optical apparatus is not restricted to an optical system of a size based on the aforementioned numerical data. The aforementioned numerical data can be reduced or enlarged appropriately. A reduced or enlarged optical system may be used for the optical apparatus. The optical system can be used as an image reducing optical system and an image magnifying optical system.

An example of an optical system that carries out magnified image pickup, having a layout in which a sample is disposed farther from a focal position, using a reduced version of the single focal length lens at the time of focusing to an object at infinity according to the example 1.

Figure 14:
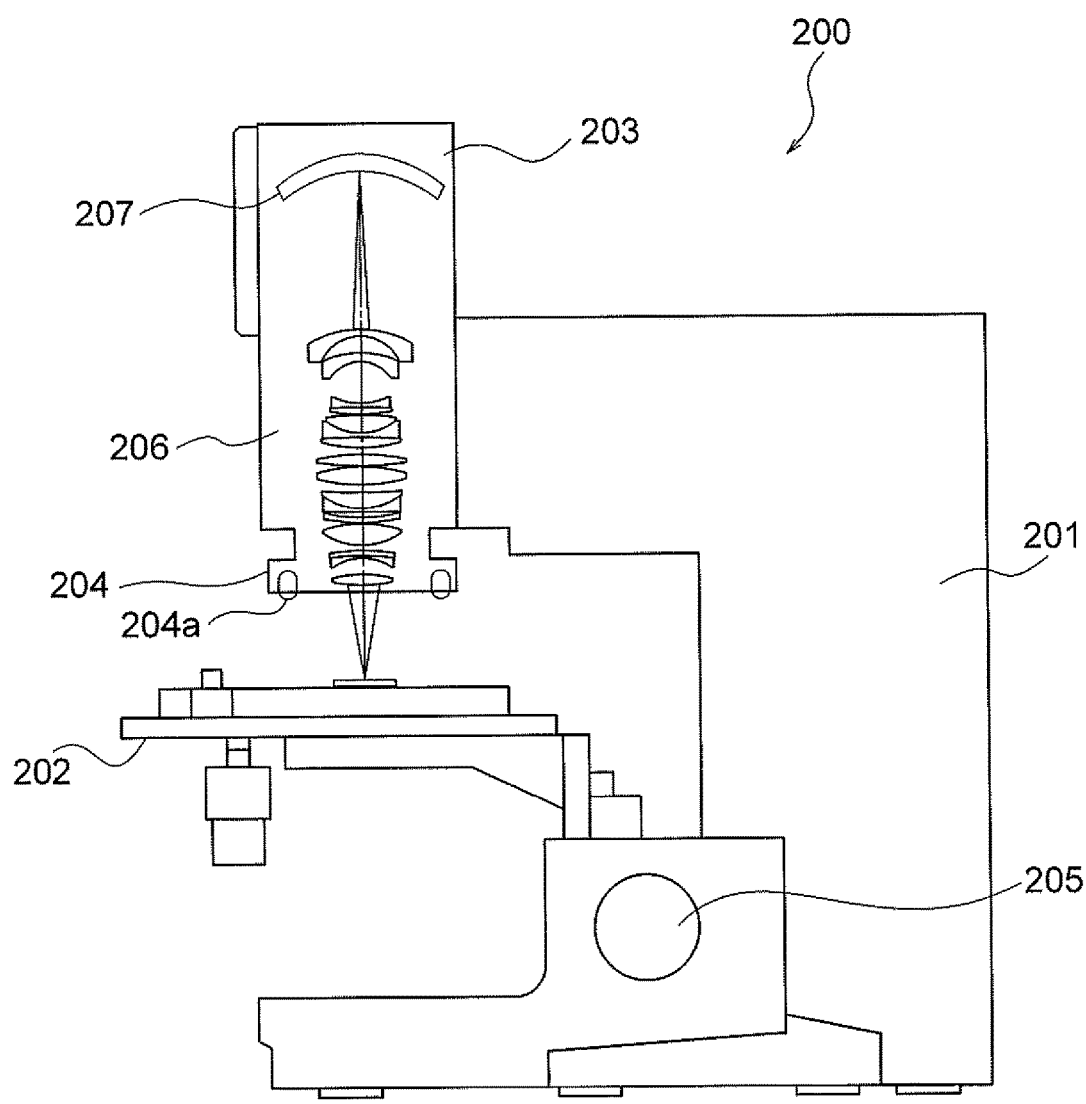
FIG. 14 is a cross-sectional view of a microscope.

FIG. 14 is a diagram showing a digital microscope which is an optical instrument of the present embodiment. A microscope 200 is a microscope of an upright type. As shown in FIG. 14, the microscope 200 includes a main body 201, a stage 202 which is movable in a horizontal direction (ex. frontward and rearward, as well as leftward and rightward) and in a vertical direction, an image pickup unit 203, an illumination unit 204, an aiming knob 205, an optical system 206, and an image pickup element 207.

The main body 201 is provided with the stage 202, the image pickup unit 203, and the aiming knob 205. A sample is to be mounted on the stage 202. The stage 202 is moved in an optical axial direction by the aiming knob 205. The stage 202 is moved by an operation (rotation) of the aiming knob 205, and accordingly, it is possible to adjust the focus on the sample. For this, a moving mechanism (not shown in the diagram) is provided between the main body 201 and the stage 3.

The image pickup unit 203 is provided with the illumination unit 204. The image pickup unit 203 and the illumination unit 204 are positioned above the stage 202. The illumination unit 204 includes illumination elements 204a disposed in annular shape. An LED (light emitting diode) is an example of the illumination element 204a.

The optical system 206 and the image pickup element 207 are disposed at an interior of the image pickup unit 203. The single focal length lens according to the example 1 for instance is used for the optical system 206. The single focal length lens includes a first lens unit, second lens unit, third lens unit, and fourth lens unit. A front end of the optical system 206 is positioned at a central portion of the illumination unit 204.

In the optical system 206, fine focusing can be performed by moving the third lens unit.

In the optical system 206, an aperture stop is disposed between the first lens unit and second lens unit. The aperture stop may be a variable aperture or a aperture in which an opening size is fixed.

From the illumination unit 204, illumination light is irradiated to a sample. In this case, the illumination is epi-illumination. Reflected light from the sample passes through the optical system 206 and is incident on the image pickup element 207. A sample image (an optical image) is formed on an image pickup surface of the image pickup element 207. The sample image is subjected to photoelectric conversion by the image pickup element 207, and accordingly, an image of the sample is acquired. The image of the sample is displayed on a display unit (not shown in the diagram). In such manner, an observer is able to observe the image of the sample.

In the optical system 206, an image plane has a curved shape. The image pickup element 207 has an image pickup surface having a curved shape along the shape of the image plane. By using the image pickup element 207, a quality of an image captured is improved.

It is possible to adjust a brightness of an optical image by the illuminating unit 204 or by adjusting an electronic-shutter speed or gain.

The microscope 200 includes the optical system 206 (the single focal length lens of the present embodiment). In the optical system 206, a value of F-number is made to be small, and various aberrations are favorably corrected brightly. Therefore, in the microscope 200, various aberrations are corrected favorably, and a bright and sharp sample image is achieved.

In the example described above, the optical system is arranged in the image pickup apparatus. However, the arrangement is not restricted to such arrangement.

Moreover, the stage 202 may be moved frontward and rearward, as well as leftward and rightward by a drive mechanism not shown in the diagram. By making such arrangement, it is possible to pick up a plurality of images by linking to a position moved to. By combining the plurality of images picked up, it is possible to achieve a captured image with high resolution over a wide photographic range.

Figure 15:
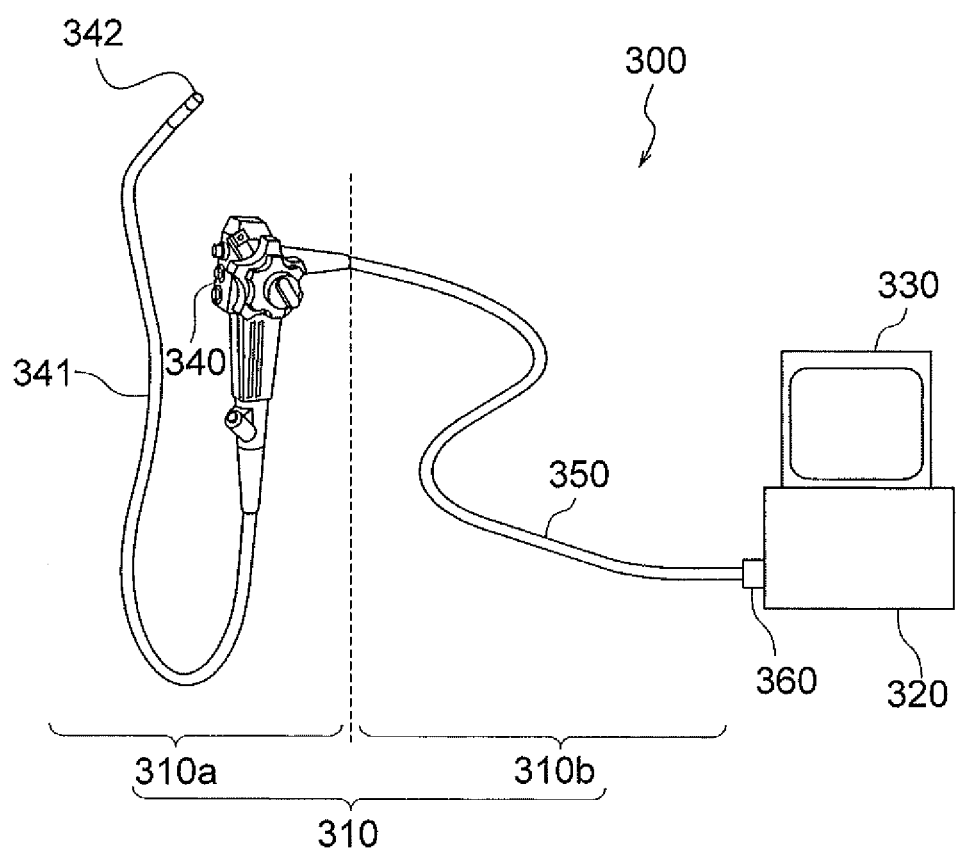
FIG. 15 is a schematic diagram of an endoscope.

An endoscope system which is an optical instrument will be described below. FIG. 15 is a diagram showing a schematic arrangement of the endoscope system.

An endoscope system 300 is an observation system in which an electronic endoscope is used. The endoscope system 300 includes an electronic endoscope 310 and an image processing unit 320. The electronic endoscope 310 includes a scope section 310a and a connecting cord section 310b. Moreover, a display unit 330 is connected to the image processing unit 320.

The scope section 310a is mainly divided into an operating portion 340 and an inserting portion 341. The inserting portion 341 is long and slender, and can be inserted into a body cavity of a patient. Moreover, the inserting portion 341 is formed of a flexible member. An observer can carry out various operations by an angle knob that is provided to the operating portion 340.

Moreover, the connecting cord section 310b is extended from the operating portion 340. The connecting cord section 301b includes a universal cord 350. The universal cord 350 is connected to the image processing unit 320 via a connector 360.

The universal cord 350 is used for transceiving of various types of signals. Various types of signals include signals such as a power-supply voltage signal and a CCD (charge coupled device) driving signal. These signals are transmitted from a power supply unit and a video processor to the scope section 310a. Moreover, various types of signals include a video signal. This signal is transmitted from the scope section 310a to the video processor.

Peripheral equipment such as a VTR (video tape recorder) deck and a video printer can be connected to the video processor inside the image processing unit 320. The video processor carries out signal processing on a video signal from the scope section 310a. On the basis of the video signal, an endoscope image is displayed on a display screen of the display unit 330.

Figure 16:
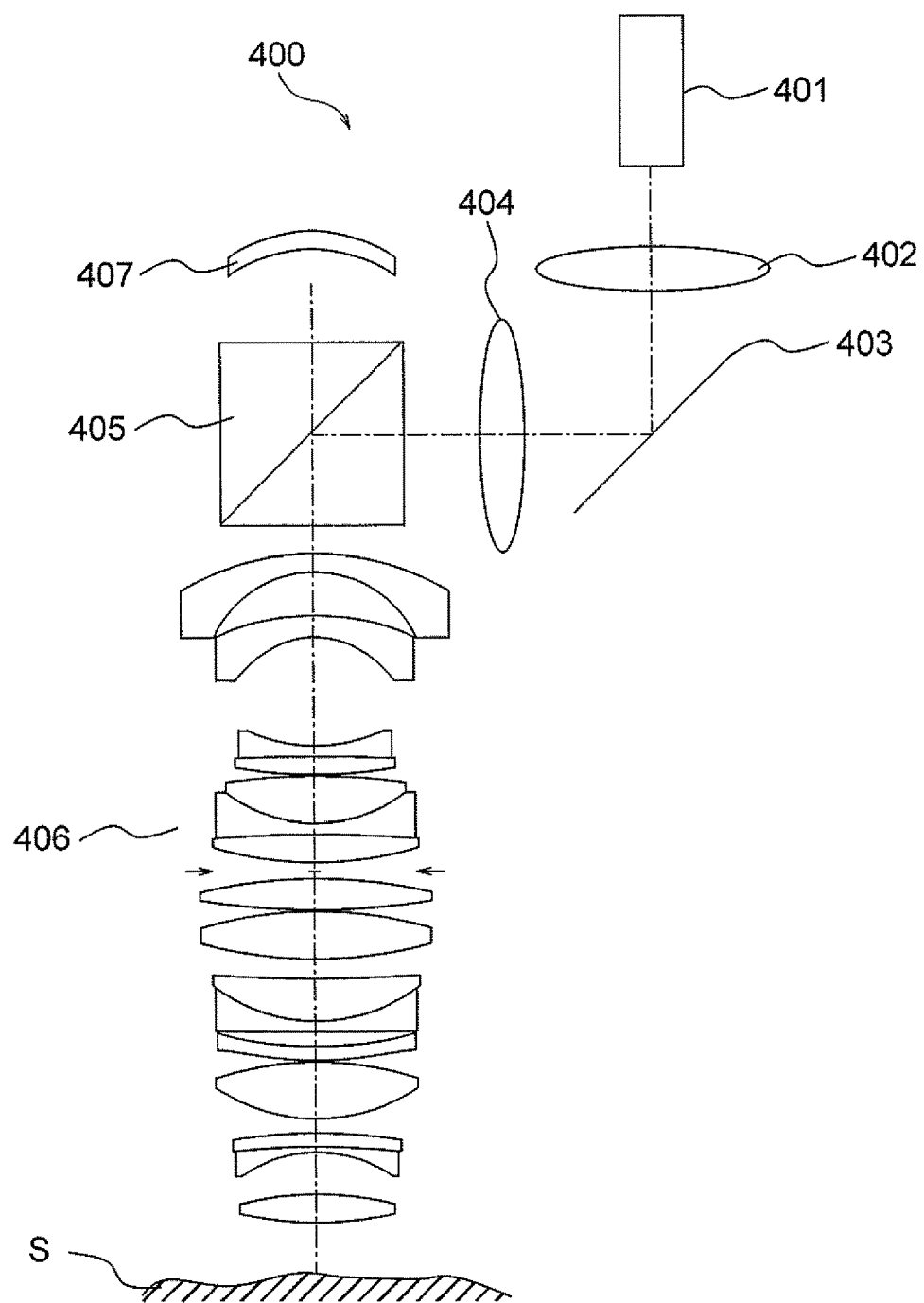
FIG. 16 is a cross-sectional view of an inserting portion.

An optical system is disposed at a front-end portion 342 of the inserting portion 341. FIG. 16 is a diagram showing an arrangement of the optical system of the endoscope. An optical system 400 includes an illuminating section and an observation section. In the optical system 400, a sample S is illuminated by epi-illumination.

The illuminating section includes a light source and an illuminating optical system. Light from the light source is emerged from an optical fiber 401. The illuminating optical system includes a lens 402, a mirror 403, a lens 404, a half prism 405, and an objective lens 406.

As the light source, a light source such as a white-light source is used. However, the light source may be let to be a light source other than the white-light source. For instance, in a case in which the sample S is a material that emits fluorescent light (such as a sample injected with a fluorescent protein or a fluorescent substance), when the light source is let to be a light source that emits excitation light having a wavelength of a narrow band, it is possible to carry out fluorescent observation of the sample S.

The observation section includes an imaging optical system and an image pickup apparatus. The imaging optical system includes an objective lens 406 and the half prism 405. The image pickup apparatus includes an image pickup element 407. For the objective lens, a lens such as the single focal length lens according to the example 1 is used.

Illumination light is irradiated to the sample from the illuminating section. In this case, the illumination is epi-illumination. Light reflected from the sample S passes through the objective lens 406 and is incident on the image pickup element 407. An image (optical image) of the sample S is formed on an image pickup surface of the image pickup element 407. The image of the sample S is subjected to opto-electric conversion by the image pickup element 407, and accordingly an image of the sample S is acquired. The image of the sample S is displayed on the display unit 330. In such manner, it is possible to observe the image of the sample S.

In the objective lens 406, an image plane has a curved shape. The image pickup element 407 has the image pickup surface having a shape curved along the shape of the image plane. By using the image pickup element 407, quality of the captured image is improved.

In an example of the digital microscope and the endoscope system, the single focal length lens of the example 1 is used as a magnification projection optical system. As a result, it is possible to acquire a favorable image in these image pickup apparatuses.

The image pickup apparatus can be let to have the following arrangements.

(A) An image pickup apparatus which includes a magnification projection optical system, and an image pickup element having a light receiving surface with a concave shape directed toward the magnification projection optical system, which is disposed on an image side of the magnification projection optical system.

(B) The image pickup apparatus described in (A), which includes a reflecting member having a reflecting surface that guides illumination light for illuminating an object into an optical path of the magnification projection optical system, between an object-side surface of incidence of the magnification projection optical system and the image pickup element.

(C) The image pickup apparatus described in (B) which includes a light-emitting source that emits illumination light.

(D) The image pickup apparatus described in (A) which includes a light emitting source that emits illumination light, outside an optical path of the magnification projection optical system.

(E) The image pickup apparatus described in one of (B), (C), and (D) in which the light-emitting source is an excitation-light source that irradiates excitation light that causes an object to emit fluorescence, as the illumination light.

According to the present invention, it is possible to provide a single focal length lens in which both of a small F-number and a wide angle of view are secured adequately, and an optical apparatus using the same.

As described above, the present invention is suitable for a single focal length lens in which both of a small F-number and a wide angle of view are secured adequately, and an optical apparatus using the same.

What is claimed is:

1. A single focal length lens comprising, in order from an object side to an image side:
    a first lens unit having a negative refractive power;
    an aperture stop;
    a second lens unit having a positive refractive power;
    a third lens unit having a negative refractive power; and
    a fourth lens unit having a positive refractive power,
    wherein:
    the single focal length lens does not include a lens unit other than the first lens unit, the second lens unit, the third lens unit, and the fourth lens unit,
    a position of the first lens unit, a position of the second lens unit, and a position of the fourth lens unit are relatively fixed in the single focal length lens, and a position of the third lens unit is relatively moveable in the single focal length lens,
    at a time of focusing from an object at infinity to an object at a short distance, the third lens unit moves toward the image side,
    the following conditional expressions (1), (2), and (3) are satisfied:

$$-5 < f1/f < -0.5 \qquad (1),$$

$$-10 < f3/f < -1 \qquad (2), \text{ and}$$

$$0.5 < f12/f < 1 \qquad (3),$$

where f1 denotes a focal length of the first lens unit, f denotes a focal length of an overall single focal length lens system at the time of focusing to an object at infinity, f3 denotes a focal length of the third lens unit, and f12 denotes a combined focal length of the first lens unit and the second lens unit,
    the first lens unit includes an object-side sub lens unit and an image-side sub lens unit,
    an air lens having a biconvex shape is formed between the object-side sub lens unit and the image-side sub lens unit,
    the object-side sub lens unit has a negative refractive power, and includes at least two negative lenses nearest to object, and
    the image-side sub lens unit includes, in order from the object side, at least one negative lens and at least one positive lens.

2. The single focal length lens according to claim 1, wherein the following conditional expression (5) is satisfied:

$$0.05 < Dm/St < 1 \qquad (5)$$

where Dm denotes a maximum variable air space from among variable air spaces in the single focal length lens, and St denotes a maximum diameter of the aperture stop.

3. The single focal length lens according to claim 1, wherein the following conditional expression (6) is satisfied:

$$0.2 < DA/DL < 1 \qquad (6)$$

where DA denotes a sum of air spaces between a lens surface nearest to the object of the single focal length lens and a lens surface nearest to an image of the single focal length lens, and DL denotes a sum of lens thicknesses between the lens surface nearest to the object of the single focal length lens and the lens surface nearest to the image of the single focal length lens.

4. An optical apparatus, comprising:
    a single focal length lens according to claim 1; and
    an image pickup element which is disposed on the image side of the single focal length lens,
    wherein the image pickup element has an image pickup surface, and converts an image formed on the image pickup surface by the single focal length lens to an electric signal.

5. An optical apparatus, comprising:
    a single focal length lens according to claim 1; and
    a display element which is disposed on the image side of the single focal length lens,
    wherein the display element has a display surface, and an image displayed on the display surface is projected toward the object side by the single focal length lens.

6. A single focal length lens comprising, in order from an object side to an image side:
    a first lens unit having a negative refractive power;
    an aperture stop;
    a second lens unit having a positive refractive power;
    a third lens unit having a negative refractive power; and
    a fourth lens unit having a positive refractive power,
    wherein:
    the single focal length lens does not include a lens unit other than the first lens unit, the second lens unit, the third lens unit, and the fourth lens unit,
    a position of the first lens unit, a position of the second lens unit, and a position of the fourth lens unit are relatively fixed in the single focal length lens, and a position of the third lens unit is relatively moveable in the single focal length lens,
    at a time of focusing from an object at infinity to an object at a short distance, the third lens unit moves toward the image side,
    the following conditional expressions (1), (2), and (3) are satisfied:

$$-5 < f1/f < -0.5 \qquad (1),$$

$$-10 < f3/f < -1 \qquad (2), \text{ and}$$

$$0.5 < f12/f < 1 \qquad (3),$$

where f1 denotes a focal length of the first lens unit, f denotes a focal length of an overall single focal length lens system at the time of focusing to an object at infinity, f3 denotes a focal length of the third lens unit, and f12 denotes a combined focal length of the first lens unit and the second lens unit,
    the second lens unit includes in order from the object side, a first sub lens unit, a second sub lens unit, and a third sub lens unit, the second lens unit does not include a sub lens unit other than the first sub lens unit, the second sub lens unit, and the third sub lens unit, the first sub lens unit has a positive refractive power, and includes at least two positive lenses, the second sub lens unit has a negative refractive power, and includes at least one negative lens, the third sub lens unit has a positive refractive power, and includes at least one positive lens, and at least one of the positive lenses in the second lens unit satisfies the following conditional expression (4):

$$80<vd2p<96 \quad (4)$$

where vd2p denotes an Abbe number for said at least one of the positive lenses in the second lens unit.

7. A single focal length lens comprising, in order from an object side to an image side:

a first lens unit having a negative refractive power;
an aperture stop;
a second lens unit having a positive refractive power;
a third lens unit having a negative refractive power; and
a fourth lens unit having a positive refractive power, wherein:

the single focal length lens does not include a lens unit other than the first lens unit, the second lens unit, the third lens unit, and the fourth lens unit, a position of the first lens unit, a position of the second lens unit, and a position of the fourth lens unit are relatively fixed in the single focal length lens, and a position of the third lens unit is relatively moveable in the single focal length lens, at a time of focusing from an object at infinity to an object at a short distance, the third lens unit moves toward the image side, the following conditional expressions (1), (2), and (3) are satisfied:

$$-5<f1/f<-0.5 \quad (1),$$

$$-10<f3/f<-1 \quad (2), \text{ and}$$

$$0.5<f12/f<1 \quad (3),$$

where f1 denotes a focal length of the first lens unit, f denotes a focal length of an overall single focal length lens system at the time of focusing to an object at infinity, f3 denotes a focal length of the third lens unit, and f12 denotes a combined focal length of the first lens unit and the second lens unit, and the following conditional expressions (7) and (8) are satisfied:

$$60°<2\omega<190° \quad (7), \text{ and}$$

$$0.8<FNOm<1.4 \quad (8),$$

where ω denotes a half angle of view at the time of focusing to an object at infinity, and FNOm denotes a minimum F-number at the time of focusing to an object at infinity.

8. A single focal length lens comprising, in order from an object side to an image side:

a first lens unit having a negative refractive power;
an aperture stop;
a second lens unit having a positive refractive power;
a third lens unit having a negative refractive power; and
a fourth lens unit having a positive refractive power, wherein:

the single focal length lens does not include a lens unit other than the first lens unit, the second lens unit, the third lens unit, and the fourth lens unit, a position of the first lens unit, a position of the second lens unit, and a position of the fourth lens unit are relatively fixed in the single focal length lens, and a position of the third lens unit is relatively moveable in the single focal length lens, at a time of focusing from an object at infinity to an object at a short distance, the third lens unit moves toward the image side, the first lens unit includes an object-side sub lens unit and an image-side sub lens unit, an air lens having a biconvex shape is formed between the object-side sub lens unit and the image-side sub lens unit, the object-side sub lens unit has a negative refractive power, and includes at least two negative lenses nearest to an object, the image-side sub lens unit includes, in order from the object side, at least one negative lens and at least one positive lens, the second lens unit includes in order from the object side, at least two positive lenses, at least one negative lens, and at least one positive lens, and at least one of the positive lenses in the second lens unit satisfies the following conditional expression (4):

$$80<vd2p<96 \quad (4)$$

where vd2p denotes an Abbe number for said at least one of the positive lenses in the second lens unit.

9. The single focal length lens according to claim 8, wherein the following conditional expression (3) is satisfied:

$$0.5<f12/f<1 \quad (3)$$

where f12 denotes a combined focal length of the first lens unit and the second lens unit, and f denotes a focal length of an overall single focal length lens system at the time of focusing to an object at infinity.

10. The single focal length lens according to claim 8, wherein the following conditional expression (5) is satisfied:

$$0.05<Dm/St<1 \quad (5)$$

where Dm denotes a maximum variable air space from among variable air spaces in the single focal length lens, and St denotes a maximum diameter of the aperture stop.

11. The single focal length lens according to claim 8, wherein the following conditional expression (6) is satisfied:

$$0.2<DA/DL<1 \quad (6)$$

where DA denotes a sum of air spaces between a lens surface nearest to the object of the single focal length lens and a lens surface nearest to an image of the single focal length lens, and DL denotes a sum of lens thicknesses between the lens surface nearest to the object of the single focal length lens and the lens surface nearest to the image of the single focal length lens.

12. The single focal length lens according to claim 8, wherein the following conditional expressions (7) and (8) are satisfied:

$$60°<2\omega<190° \quad (7), \text{ and}$$

$$0.8<FNOm<1.4 \quad (8)$$

where ω denotes a half angle of view at the time of focusing to an object at infinity, and FNOm denotes a minimum F-number at the time of focusing to an object at infinity.

13. A single focal length lens comprising, in order from a magnification side to a reduction side:
a first lens unit having a negative refractive power;
an aperture stop;
a second lens unit having a positive refractive power;
a third lens unit having a negative refractive power; and
a fourth lens unit having a positive refractive power;
wherein:
the single focal length lens does not include a lens unit other than the first lens unit, the second lens unit, the third lens unit, and the fourth lens unit,
the first lens unit, the second lens unit, and the fourth lens unit are relatively fixed in the single focal length lens, and the third lens unit is relatively moveable in the single focal length lens,
at a time of focusing, the third lens unit moves,
the first lens unit includes a magnification-side sub lens unit and a reduction-side sub lens unit,
an air lens having a biconvex shape is formed between the magnification-side sub lens unit and the reduction-side sub lens unit,
the magnification-side sub lens unit has a negative refractive power, and includes at least two negative lenses on the farthest magnification side,
the reduction-side sub lens unit includes, in order from the magnification side, at least one negative lens and at least one positive lens,
the second lens unit includes, in order from the magnification side, at least two positive lenses, at least one negative lens, and at least one positive lens, and
at least one of the positive lenses in the second lens unit satisfies the following conditional expression (4):

$$80 < vd2p < 96 \qquad (4)$$

where vd2p denotes an Abbe number for said at least one of the positive lenses in the second lens unit.

14. The single focal length lens according to claim 13, wherein the following conditional expression (5) is satisfied:

$$0.05 < Dm/St < 1 \qquad (5)$$

where Dm denotes a maximum variable air space from among variable air spaces in the single focal length lens, and St denotes a maximum diameter of the aperture stop.

15. An optical apparatus, comprising:
a single focal length lens according to claim 13; and
an image pickup element which is disposed on an image side of the single focal length lens,
wherein the image pickup element has an image pickup surface, and converts an image formed on the image pickup surface by the single focal length lens to an electric signal.

* * * * *

UNITED STATES PATENT AND TRADEMARK OFFICE
CERTIFICATE OF CORRECTION

PATENT NO. : 10,073,255 B2
APPLICATION NO. : 15/494687
DATED : September 11, 2018
INVENTOR(S) : Masaru Morooka et al.

It is certified that error appears in the above-identified patent and that said Letters Patent is hereby corrected as shown below:

In the Specification

Column 5, Line 6, after "power" insert --of--.

Column 8, Line 5, after "light" insert --ray--.

Column 9, Line 66, delete "minimum," and insert --minimum--.

Column 13, Line 31, delete "failing" and insert --falling--.

Column 15, Line 59, after "astigmatism" insert --(AS)--.

Column 16, Line 2, after "having" insert --a--.

Column 19, Line 25, delete "Various" and insert --various--.

Column 25, Line 17, delete "protection" and insert --projection--.

Column 26, Line 40, delete "SCRAM" and insert --SDRAM--.

Column 26, Line 57, after "display" insert --section--.

Column 30, Line 28, after "sample" insert --S--.

Signed and Sealed this
Eleventh Day of December, 2018

Andrei Iancu
*Director of the United States Patent and Trademark Office*